(12) United States Patent
Schultz

(10) Patent No.: US 9,572,958 B2
(45) Date of Patent: *Feb. 21, 2017

(54) CATHETER WITH MULTI-FUNCTIONAL CONTROL HANDLE HAVING ROTATIONAL MECHANISM

(71) Applicant: Biosense Webster, Inc., Diamond Bar, CA (US)

(72) Inventor: Jeffrey William Schultz, Chino, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,140

(22) Filed: May 18, 2015

(65) Prior Publication Data

US 2015/0246206 A1 Sep. 3, 2015

Related U.S. Application Data

(63) Continuation of application No. 12/550,307, filed on Aug. 28, 2009, now Pat. No. 9,033,916.

(51) Int. Cl.
*A61M 31/00* (2006.01)
*A61M 25/01* (2006.01)
(Continued)

(52) U.S. Cl.
CPC ....... *A61M 25/0147* (2013.01); *A61B 5/0422* (2013.01); *A61B 5/6857* (2013.01);
(Continued)

(58) Field of Classification Search
CPC .......... A61B 18/1492; A61B 2017/003; A61B 2018/00351; A61M 25/0136; A61M 25/0147; A61M 25/0133
(Continued)

(56) References Cited

U.S. PATENT DOCUMENTS

RE34,502 E 1/1994 Webster, Jr.
5,531,686 A 7/1996 Lundquist et al.
(Continued)

FOREIGN PATENT DOCUMENTS

CN 101304778 A 11/2008
EP 1 457 225 A2 9/2004
(Continued)

OTHER PUBLICATIONS

European Search Report dated Nov. 15, 2010, issued in EP10251506, 6 pages.
(Continued)

*Primary Examiner* — Joseph Stoklosa
*Assistant Examiner* — Brian M Antiskay
(74) *Attorney, Agent, or Firm* — Lewis Roca Rothgerber Christie LLP

(57) ABSTRACT

A catheter for use in a patient's heart, especially for mapping a tubular region of the heart, has a catheter body, a deflectable intermediate section and a distal mapping assembly that has a generally circular portion adapted to sit on or in a tubular region of the heart. A control handle of the catheter allows for single-handed manipulation of various control mechanisms that can deflect the intermediate section and contract the mapping assembly by means of a deflection control assembly and a rotational control assembly. The deflection control assembly has a deflection arm and a rocker member. The rotational control assembly has an outer rotational member, an inner rotational member and a cam. A pair of puller members are responsive to the deflection control assembly to bi-directionally deflect the intermediate section. A third puller member is responsive to the rotational control assembly to contract the generally circular portion of the mapping assembly.

22 Claims, 25 Drawing Sheets

(51) Int. Cl.
*A61B 5/042* (2006.01)
*A61B 5/00* (2006.01)
*A61B 18/08* (2006.01)
A61B 5/04 (2006.01)
A61B 18/18 (2006.01)
A61N 1/00 (2006.01)

(52) U.S. Cl.
CPC ....... *A61B 18/082* (2013.01); *A61M 25/0136* (2013.01); *A61M 2025/015* (2013.01); *A61M 2025/0161* (2013.01); *A61M 2210/125* (2013.01); *A61M 2230/04* (2013.01)

(58) Field of Classification Search
USPC ............. 600/372, 381, 466; 604/95.04, 528; 606/41–50; 607/101–102, 122
See application file for complete search history.

(56) References Cited

U.S. PATENT DOCUMENTS

| | | |
|---|---|---|
| 5,545,200 A | 8/1996 | West et al. |
| 5,957,961 A | 9/1999 | Maguire et al. |
| 5,987,344 A | 11/1999 | West |
| 6,123,699 A | 9/2000 | Webster, Jr. |
| 6,171,277 B1 | 1/2001 | Ponzi |
| 6,183,463 B1 | 2/2001 | Webster, Jr. |
| 6,263,224 B1 | 7/2001 | West |
| 6,491,681 B1 | 12/2002 | Kunis et al. |
| 6,571,131 B1 * | 5/2003 | Nguyen ........................ 607/122 |
| 6,913,594 B2 | 7/2005 | Coleman et al. |
| 7,274,957 B2 | 9/2007 | Drysen |
| 7,931,616 B2 | 4/2011 | Selkee |
| 2005/0119721 A1 | 6/2005 | Rabkin et al. |
| 2005/0277875 A1 | 12/2005 | Selkee |
| 2005/0288656 A1 | 12/2005 | Koerner et al. |
| 2007/0066878 A1 | 3/2007 | Worley et al. |
| 2008/0009882 A1 | 1/2008 | Drysen |
| 2008/0103520 A1 | 5/2008 | Selkee |
| 2010/0069834 A1 | 3/2010 | Schultz |
| 2010/0168827 A1 | 7/2010 | Schultz |

FOREIGN PATENT DOCUMENTS

| | | |
|---|---|---|
| JP | 2006-000649 | 1/2006 |
| WO | WO 2007/002713 A2 | 1/2007 |

OTHER PUBLICATIONS

English Translation of Japanese Office Action dated Mar. 4, 2014, corresponding to Application No. 2010-190475, 3 pages.
SIPO Search Report dated Jul. 2, 2013 for CN 201010267393.4 with English translation (3 pages).
English translation of SIPO Office action dated Jul. 2, 2013 for CN 201010267393.4 (9 pages).

* cited by examiner

CATHETER WITH MULTI-FUNCTIONAL CONTROL HANDLE HAVING ROTATIONAL MECHANISM

CROSS-REFERENCE TO RELATED APPLICATION(S)

This application a continuation of and claims priority to and the benefit of U.S. application Ser. No. 12/550,307 filed Aug. 28, 2009, now U.S. Pat. No. 9,033,916, the entire disclosure of which is incorporated herein.

FIELD OF INVENTION

This invention relates to a catheter, in particular, a catheter with a control handle having multiple control mechanisms for deflecting and contracting portions of the catheter.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements that include deflection of a distal portion of the catheter so that the mapping assembly is positioned at the tubular region in the heart chamber. The ability to control the exact position and orientation of the catheter and also the configuration of the mapping assembly is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If bi-directional deflection is desire, more than one puller wire becomes necessary. Moreover, if more control is desired, such as contraction of the mapping assembly, an additional puller wire is needed. Space is limited within a control handle and operation of puller wire control mechanisms must not interfere with components that extend through the control handle, such as lead wires, cables, and irrigation tubing. Moreover, it is desirable that the control mechanisms be arranged such that the catheter can be operated single-handedly by the user. Accordingly, a need exists for a control handle capable of moving three puller wires for at least two independent movements, such as bi-directional deflection of the catheter shaft and contraction of the mapping assembly, preferably through a single-handed manipulation of the user.

SUMMARY OF THE INVENTION

The present invention is directed to a catheter for use in a patient's heart, especially for mapping a tubular region of the heart. In one embodiment, the catheter has a catheter body and a deflectable intermediate section distal the catheter body. Distal the intermediate section is a mapping assembly that has a generally circular portion adapted to sit on or in a tubular region of the heart. A control handle of the catheter allows for single-handed manipulation of various control mechanisms that can deflect the intermediate section and contract the mapping assembly by means of a deflection control assembly and a rotational control assembly. The deflection control assembly has a deflection arm and a rocker member. The rotational control assembly has an outer rotational member, an inner rotational member and a cam. A pair of puller members are responsive to the deflection control assembly to bi-directionally deflect the intermediate section. A third puller member is responsive to the rotational control assembly to contract the generally circular portion of the mapping assembly.

In a more detailed embodiment, a proximal end of the third puller member is anchored in the rotational control assembly, such that rotation of the outer rotational member by a user moves the third puller member longitudinally relative to the catheter body. The outer rotational member generally surrounds the inner rotational member and the inner rotational member is rotatably mounted on the cam. The control assembly includes a follower to which a proximal end of the third puller member is anchored and the follower is adapted to follow the movement of the inner rotational member so as to slide in a track formed on the cam. In a more detailed embodiment, the track is helical on the cam, and the outer and inner rotational members are rotationally coupled by formations, that include interlocking teeth or fingers that engage holes.

The rotational control assembly can be arranged such that the inner rotational member and the outer rotational member have a common rotational axis, or different rotational axes. Moreover, the rotational control assembly can be located either proximally or distally of the deflection control assembly. The control handle can include a tension control assembly adapted to adjust tension of the deflection control assembly.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

DETAILED DESCRIPTION OF THE INVENTION

Figure 1:
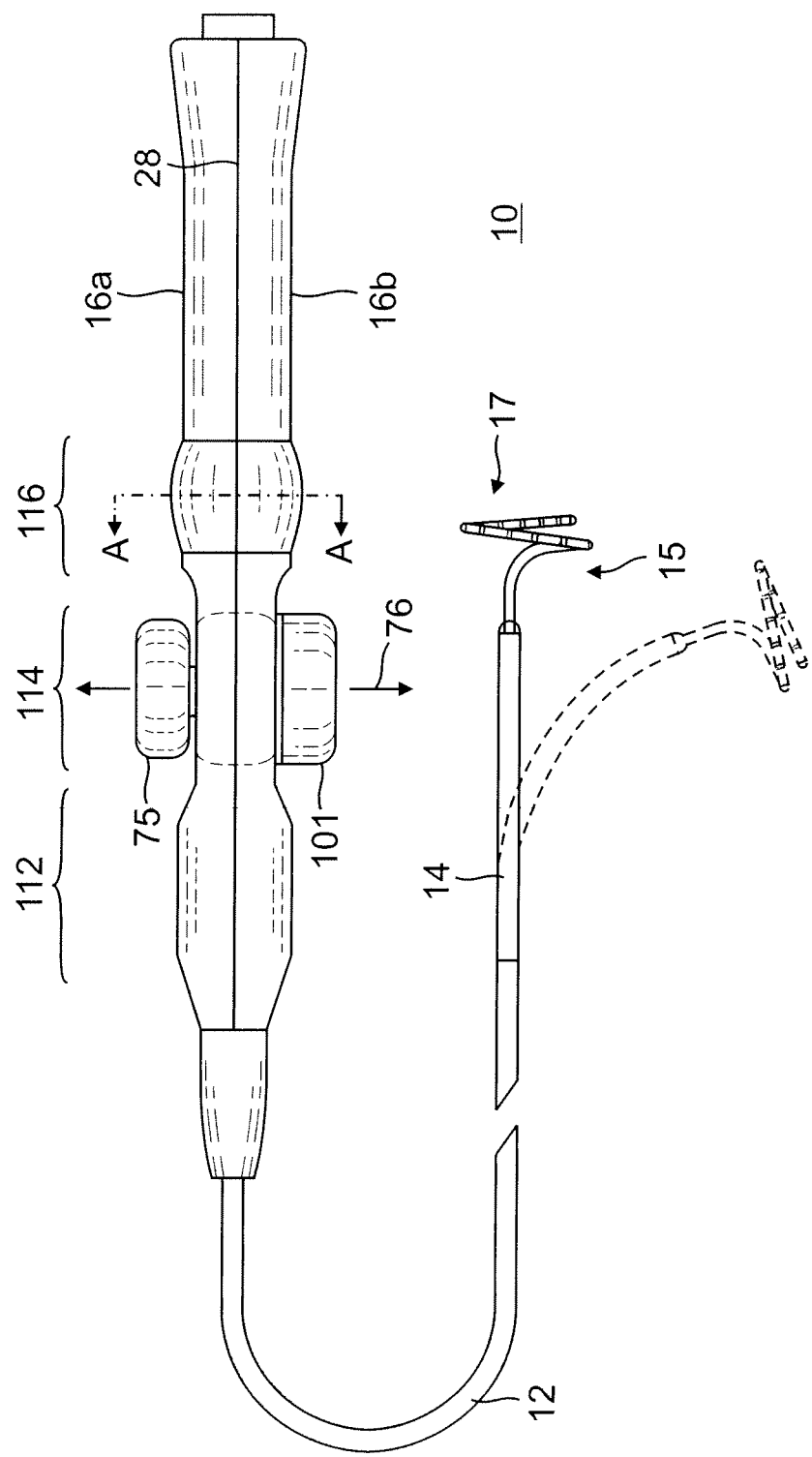
FIG. 1 is a top plan view of one embodiment of the catheter of the present invention.

Referring to FIG. 1, the present invention is directed to a catheter 10 with multiple control capabilities for mapping and/or ablation of the heart. In the illustrated embodiment of FIG. 1, a catheter 10 comprises an elongated catheter body 12, a deflectable intermediate section 14 at a distal end of the catheter body 12, a tip section 15 including a mapping assembly 17 at a distal end of the intermediate section 14, and a multi-functional control handle 16 at a proximal end of the catheter body 12 for controlling portions of the catheter, for example, deflecting the intermediate section 14 and contracting the mapping assembly 17.

Figure 2A:
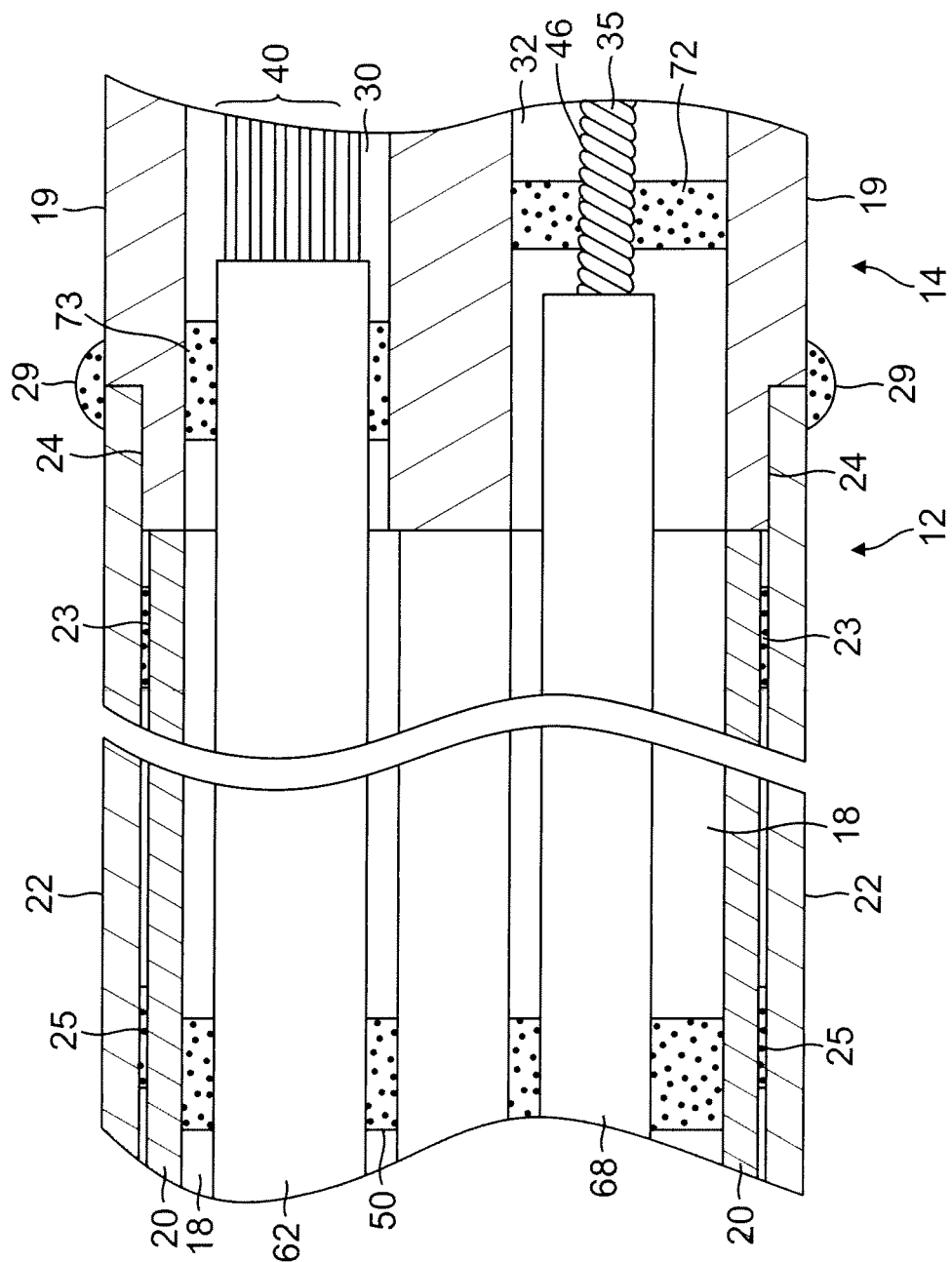
FIG. 2a is a side cross-sectional view of an embodiment of a junction of a catheter body and an intermediate section, taken along a first diameter.
Figure 2B:
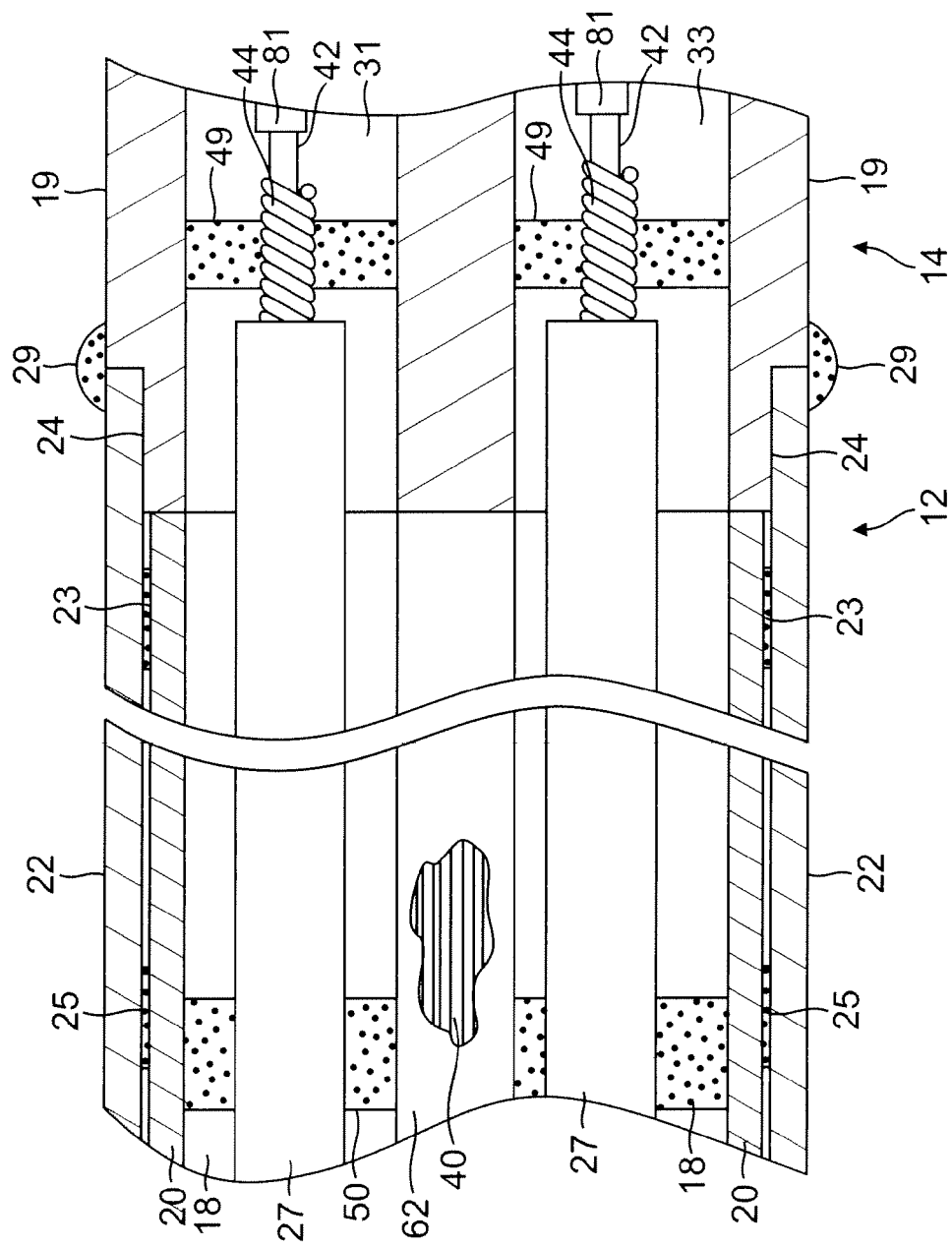
FIG. 2b is a side cross-sectional view of the embodiment of the junction of FIG. 2a, taken along a second diameter generally perpendicular to the first diameter.

With reference to FIGS. 2A and 2B, the catheter body 12 comprises a single, central or axial lumen 18. The catheter body 12 is flexible, i.e., bendable, but substantially non-compressible along its length. The catheter body 12 may be of any suitable construction and made of any suitable material. A suitable construction comprises an outer wall 22 made of a polyurethane or nylon. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, e.g., polyimide. The stiffening tube 20 is held in place relative to the outer wall 22 at the proximal end of the catheter body 12. A first glue joint 23 is made between the distal ends of the stiffening tube 20 and the outer wall 22 by a fast drying glue, e.g. Super Glue®. Thereafter a second glue joint 25 is formed between the proximal ends of the stiffening tube 20 and outer wall 22 using a slower drying but stronger glue, e.g., polyurethane.

The stiffening tube, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, nylon or other similar material, particularly having a stainless steel braided mesh, the tendency for the polyimide stiffening tube 20 to kink when bent is essentially eliminated with respect to the applications for which the catheter is used.

In one embodiment, the outer wall 22 has an outer diameter of about 0.092 inch and an inner diameter of about 0.063 inch and the polyimide stiffening tube 20 has an outer diameter of about 0.0615 inch and an inner diameter of about 0.052 inch.

Figure 4:
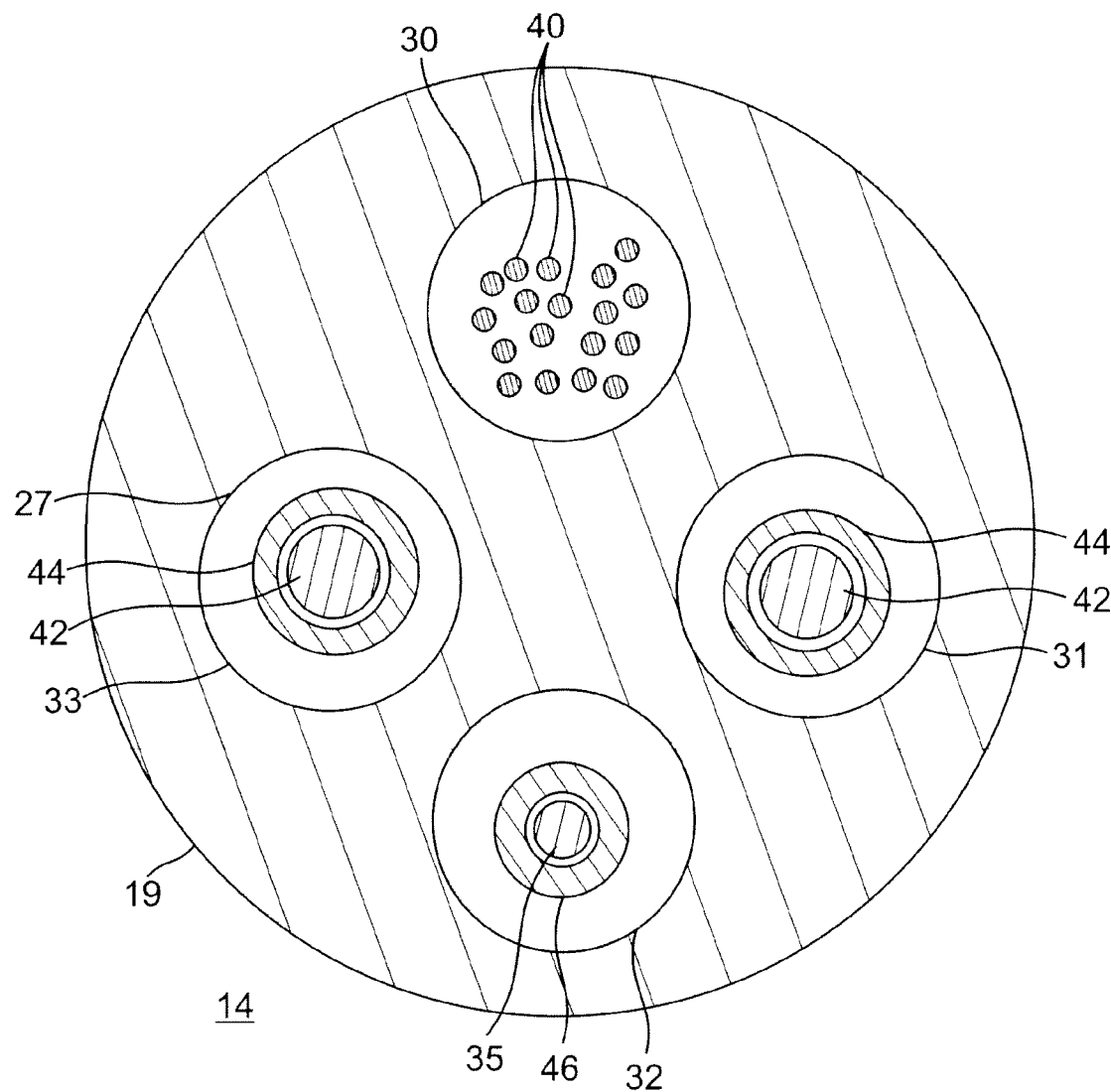
FIG. 4 is a longitudinal cross-sectional view of the intermediate section of FIG. 3, taken along line 4-4.

As shown in FIGS. 2A, 2B and 4, the intermediate section 14 comprises a shorter section of tubing 19 with multiple off-axis lumens, for example, first, second, third and fourth lumens 30, 31, 32 and 33. The tubing 19 is made of a suitable non-toxic material which is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch) and the lumens are generally about the same size, having a diameter of about 0.022 inch, or selected lumens can have a slightly larger diameter of about 0.036 inch.

A means for attaching the catheter body 12 to the intermediate section 14 is illustrated in FIGS. 2A and 2B. The proximal end of the intermediate section 14 comprises an inner counter bore 24 that receives the outer surface of the polyimide stiffener 20. The intermediate section 14 and catheter body 12 are attached by glue 29 or the like.

As shown in FIGS. 2A and 2B, extending through the single lumen 18 of the catheter body 12 are various components, for example, lead wires and multiple puller members, and any other wires or cables. Longitudinal movement of the puller members relative to the catheter body 12 enable user control of various parts of the catheter via the control handle. In one embodiment, the puller members include a pair of deflection puller members 42 for deflecting the intermediate section 14 and a contraction puller member 35 for adjusting the mapping assembly 17 of the tip section 15.

A single lumen catheter body 12 can be preferred over a multi-lumen body because the single lumen 18 body can permit better tip control when rotating the catheter 10. The single lumen 18 permits the components passing therethrough to float freely within the catheter body. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

Figure 8A:
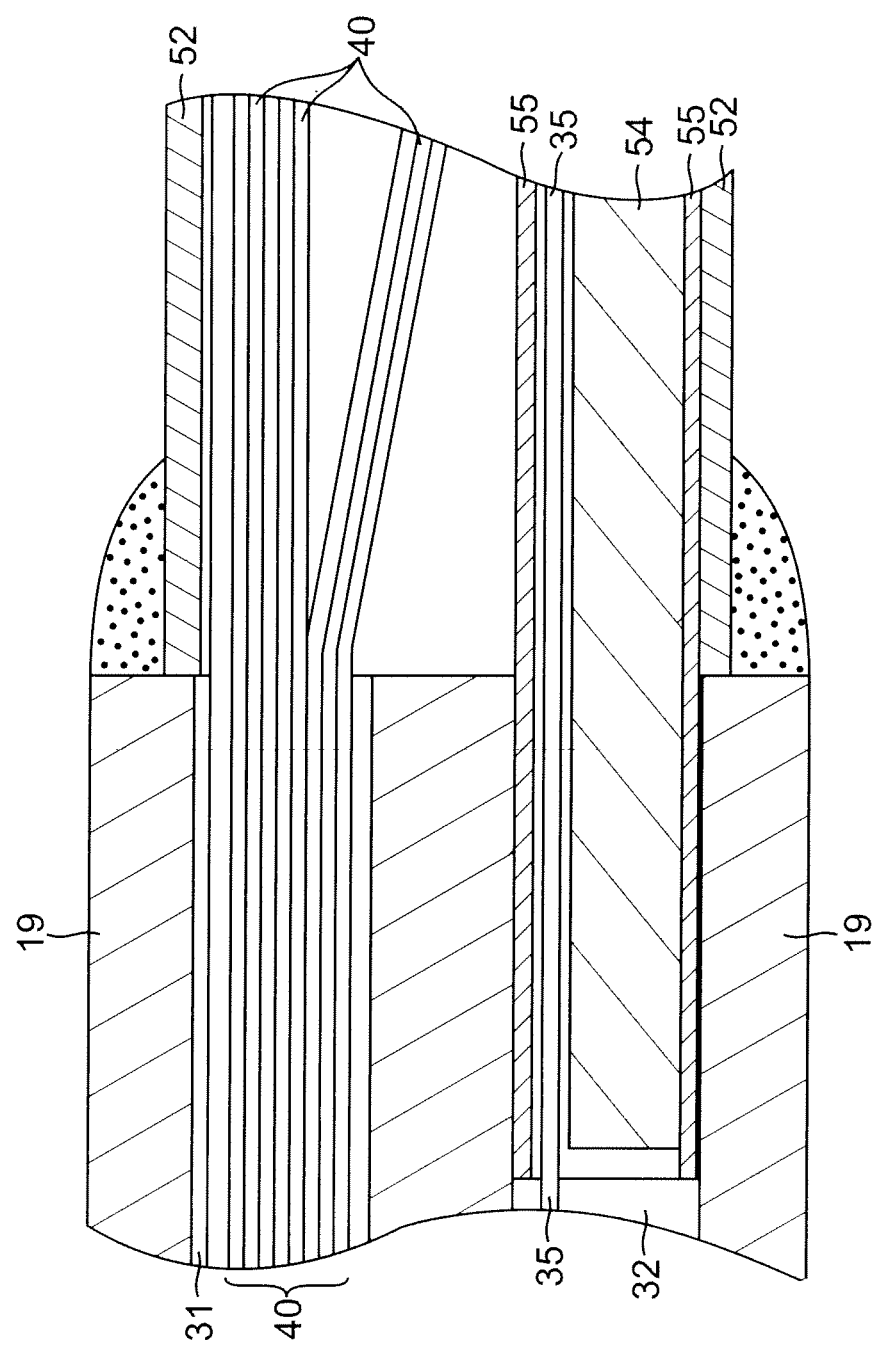
FIG. 8a is a side cross-sectional view of an embodiment of a junction between the intermediate section and the mapping assembly, taken along a first diameter.
Figure 8B:
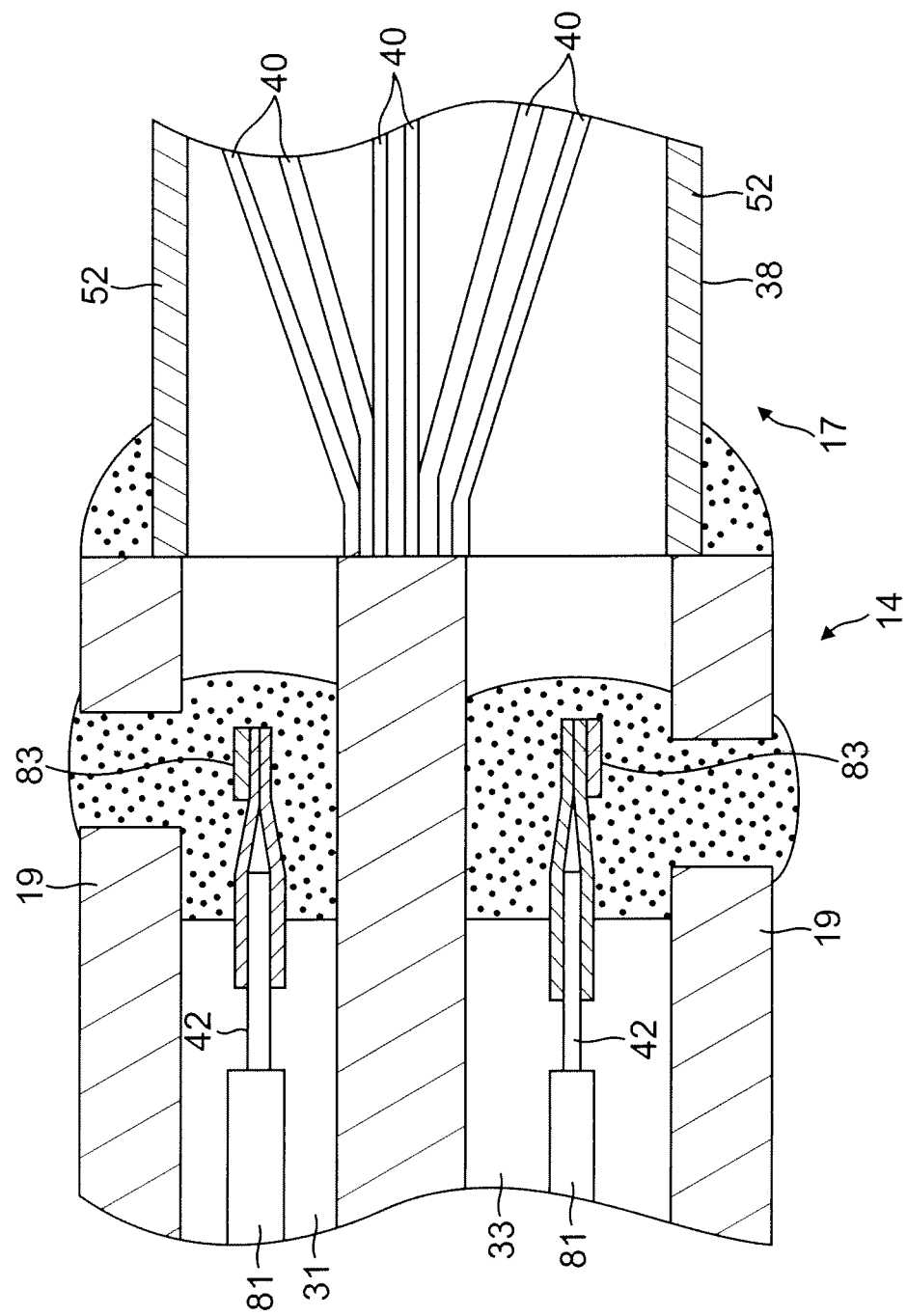
FIG. 8b is a side cross-sectional view of an embodiment of a junction between the intermediate section and the mapping assembly, taken along a second diameter generally perpendicular to the first diameter.

A deflection puller member 42 extends through the central lumen 18 of the catheter body 12 and into the second lumen 31 of the intermediate section 14. Another deflection puller member 42 extends through the central lumen 18 and into the fourth lumen 33 of the intermediate section 14. The distal ends of the deflection puller members 42 are anchored to the wall of the tubing 19 near the distal end of the intermediate section 14 by means of T-anchors 83 (FIG. 8B). In the intermediate section 14, each deflection puller members 42 extends through a plastic, e.g., Teflon®, sheath 81, which prevents the deflection puller members 42 from cutting into the wall of the tubing 19 of the intermediate section 14 when the intermediate section 14 is deflected.

As shown in FIG. 2B, compression coils 44 in surrounding relation to the deflection puller members 42 extend from the proximal end of the catheter body 12 to the proximal end of the intermediate section 14. The compression coils 44 are made of any suitable metal, e.g., stainless steel. The compression coils 44 are tightly wound on itself to provide flexibility, i.e., bending, but to resist compression. The inner diameter of the compression coils 44 is preferably slightly larger than the diameter of the puller wires 42. For example, when a puller member 42 has a diameter of about 0.007 inches, the compression coil 44 preferably has an inner diameter of about 0.008 inches. The Teflon® coating on the puller member 42 allows them to slide freely within the compression coils 44. The outer surface of the compression coils 44 is covered by a flexible, non-conductive sheath 27 to prevent contact between the compression coils 44 and other components, such as lead wires and cables, etc. A non-conductive sheath can be made of polyimide tubing.

The compression coils 44 are anchored at their proximal ends to the proximal end of the stiffening tube 20 in the catheter body 12 by glue joint 50 (FIG. 2B) and at its distal end near the proximal end of the intermediate section 14 in the second lumen 31 and fourth lumen 33 by glue joints 49 (FIG. 2B).

Figure 3:
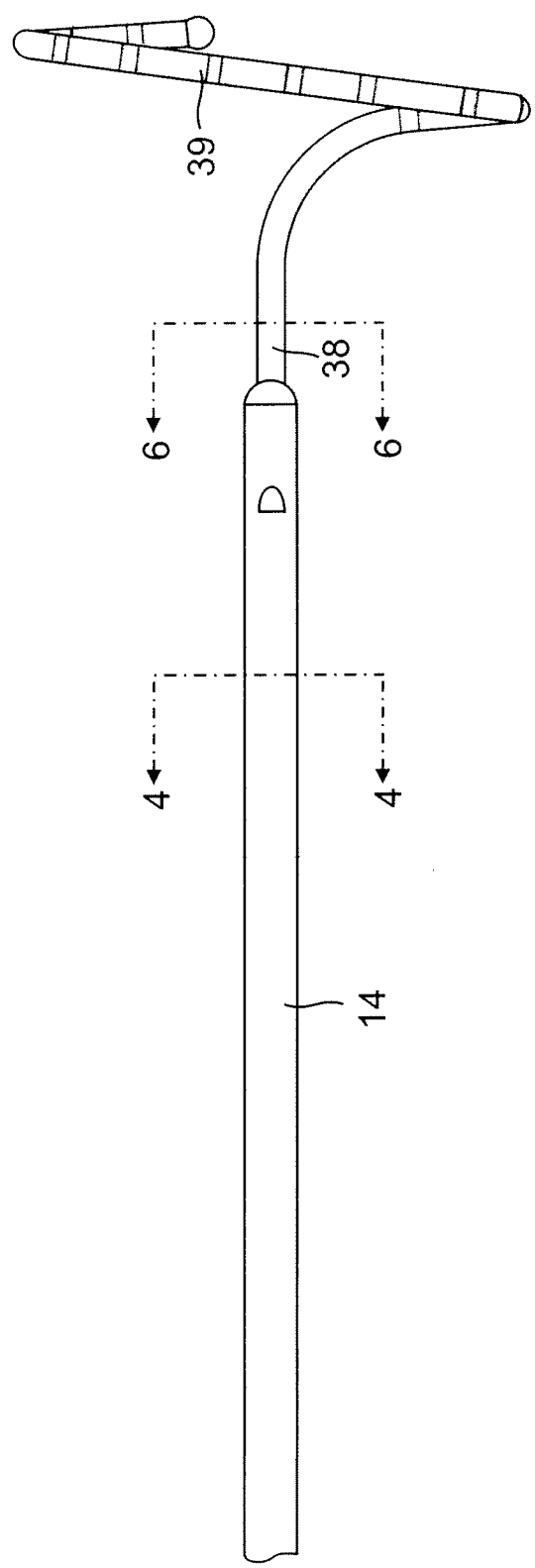
FIG. 3 is a side view of a distal portion of the catheter of FIG. 1, including an intermediate section and a mapping assembly.

With reference to FIG. 3, at the distal end of the intermediate shaft 14 is the mapping assembly 17. The mapping assembly 17 comprises a generally straight proximal region 38 and a generally circular main region 39. The proximal region 38 is mounted on the intermediate section 14, as described in more detail below, so that it is generally a linear extension of the intermediate section 14. In one embodiment, the proximal region 38 has an exposed length, e.g., not contained within the intermediate section 14, ranging from about 3 mm to about 12 mm, more preferably about 3 mm to about 8 mm, still more preferably about 5 mm, but can vary as desired.

Figure 5:
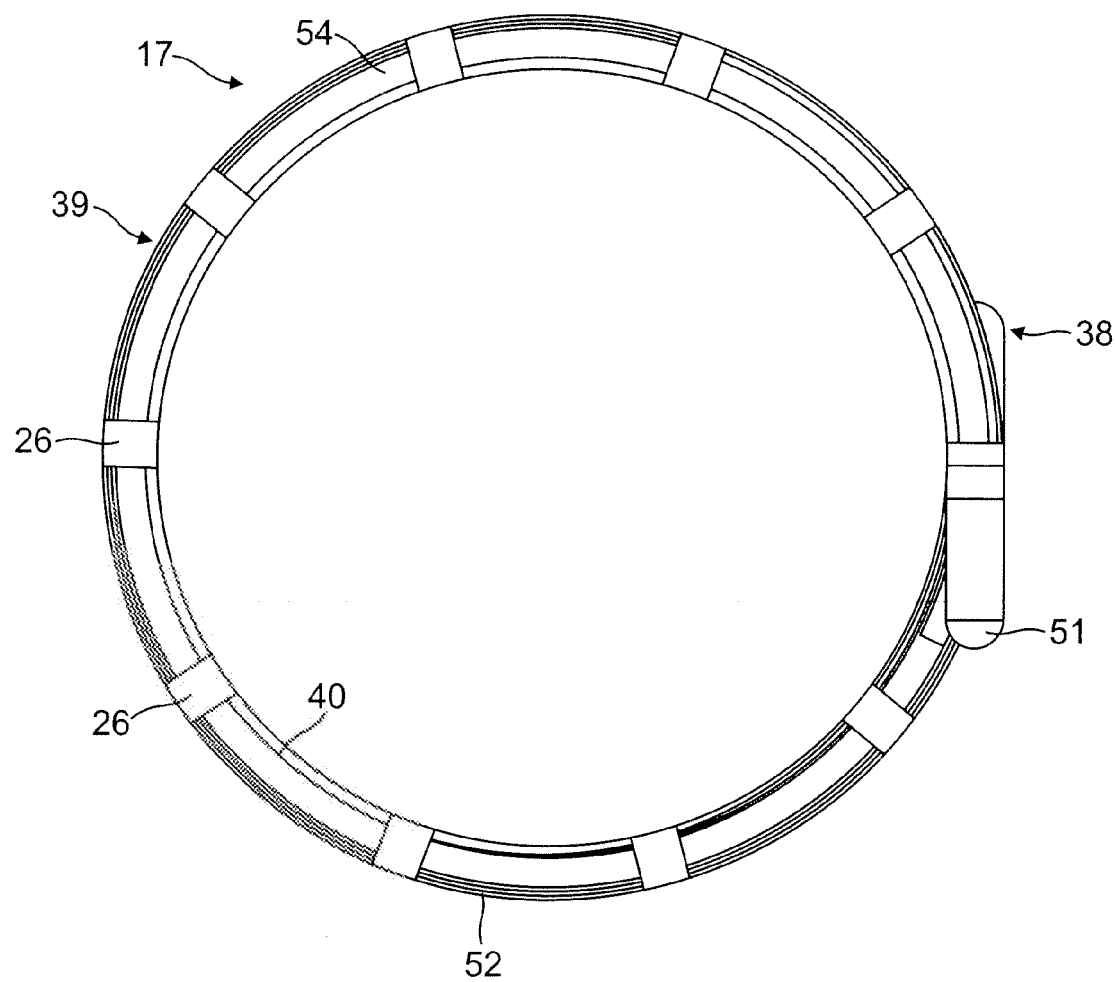
FIG. 5 is a schematic view of the mapping assembly showing one arrangement of the ring electrodes.
Figure 6:
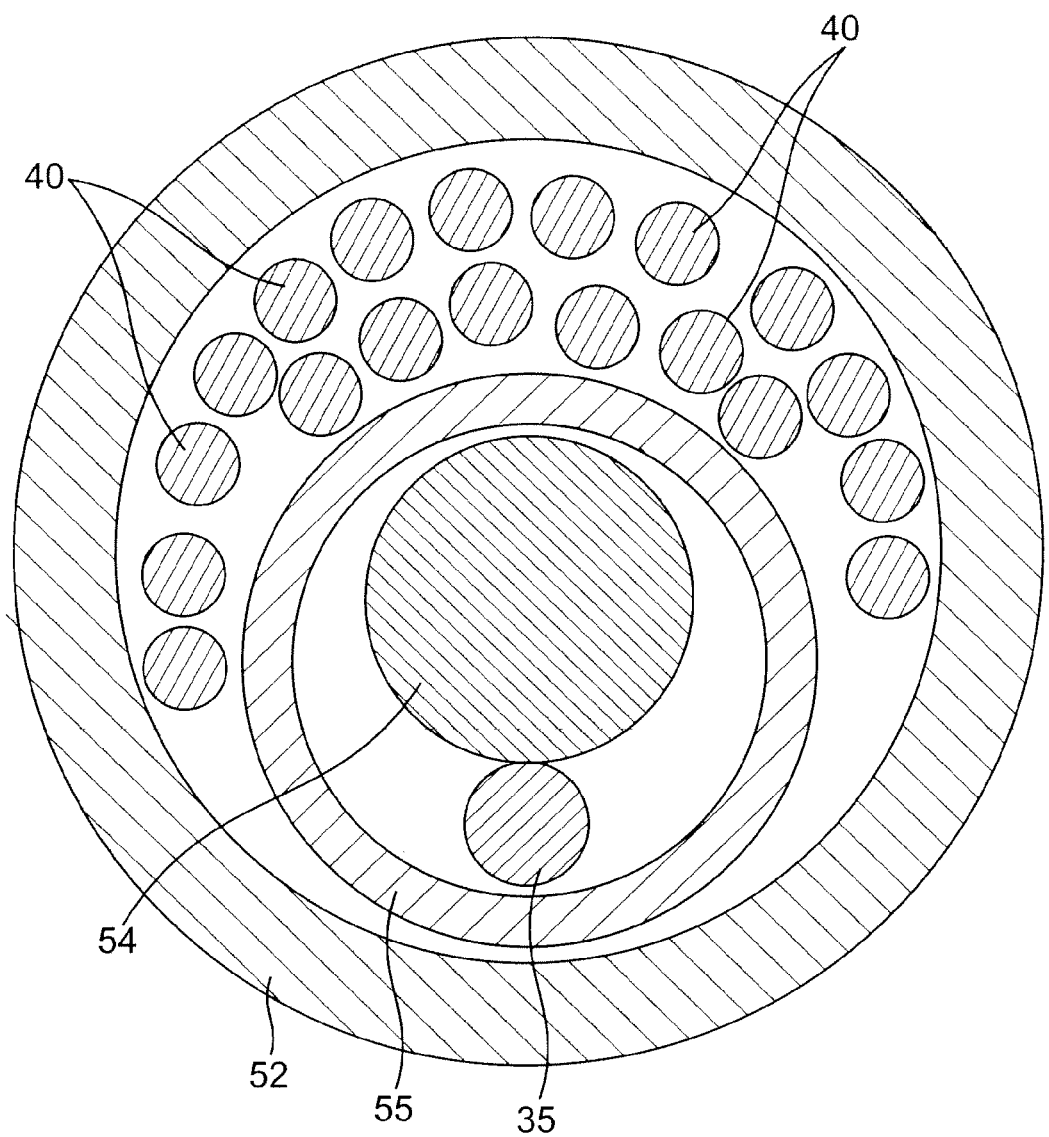
FIG. 6 is a longitudinal cross-sectional view of the mapping assembly of FIG. 3 along line 6-6.
Figure 7:
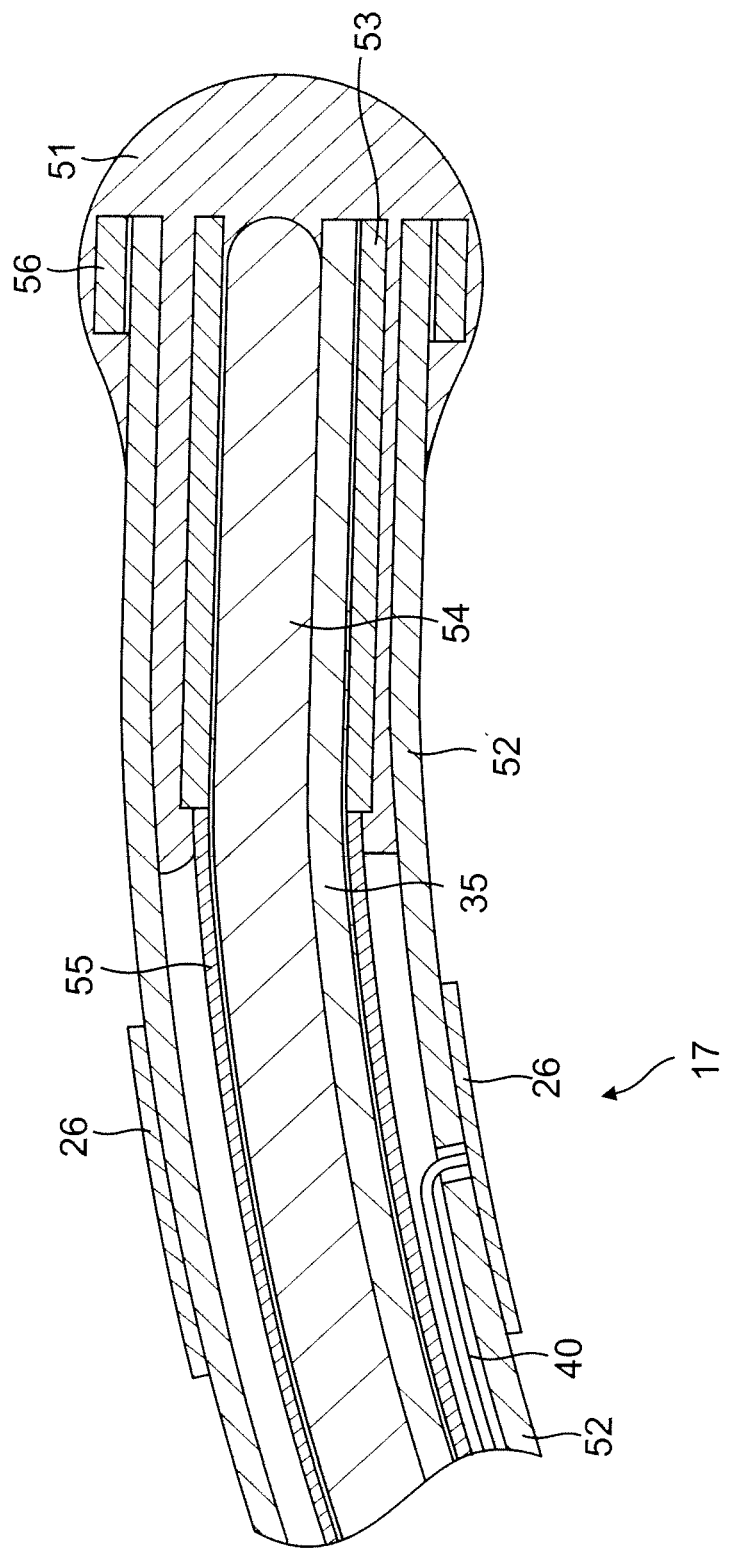
FIG. 7 is a side cross-sectional view of an embodiment of a distal end of the mapping assembly of FIG. 3.

The generally circular main region 39 is generally traverse, if not also perpendicular, to the catheter body 12. The generally circular main region 39 can form a flat circle or can be very slightly helical. In one embodiment, the main region 39 has an outer diameter ranging from about 10 mm to about 25 mm, more preferably about 12 mm to about 20 mm. The generally circular main region 39 can curve in a clockwise direction or a counterclockwise direction. As shown in FIGS. 5, 6 and 7, the mapping assembly 17 is formed of a non-conductive cover or tubing 52 which can have any cross-sectional shape as desired. The non-conductive cover 52 can be made of any suitable material, and is preferably made of a biocompatible plastic such as polyurethane or PEBAX. The non-conductive cover 52 can be pre-formed into the desired generally circular shape of the generally circular main region 39. Alternatively, the shape of the generally circular main region 39 can be defined by a wire or other component extending through the non-conductive cover 52.

In the depicted embodiment, a pre-formed support member 54 extends through the non-conductive cover 52 to define the shape of the generally circular main region 39. The support member 54 is made of a material having shape-memory, i.e., that can be straightened or bent out of its original shape upon exertion of a force and is capable of substantially returning to its original shape upon removal of the force. On suitable material for the support member 54 is a nickel/titanium alloy. Such alloys typically comprise about 55% nickel and 45% titanium, but may comprise from about 54% to about 57% nickel with the balance being titanium. A suitable nickel/titanium alloy is Nitinol, which has excellent shape memory, together with ductility, strength, corrosion resistance, electrical resistivity and temperature stability.

A series of ring electrodes 26 are mounted on the non-conductive cover 52 of the generally circular main region 39 of the mapping assembly 17, as shown in FIG. 5. The ring electrodes 26 can be made of any suitable solid conductive material, such as platinum or gold, or a combination of platinum and iridium, and mounted onto the non-conductive cover 52 with glue or the like. Alternatively, the ring electrodes 26 can be formed by coating the non-conductive cover 52 with an electrically conducting material, like platinum, gold and/or iridium. The coating can be applied using sputtering, ion beam deposition or an equivalent technique. A suitable mapping assembly is described in U.S. Pat. No. 7,274,957, the entire disclosure of which is hereby incorporated by reference. If desired, additional electrodes (not shown) could be mounted along the intermediate section 14 and/or the generally straight proximal section 38.

The contraction puller member 35, for example, a contraction puller wire, is provided to contract the generally circular main region 39 to thereby change or reduce its diameter, for example, when mapping or ablating circular or tubular regions of the heart. The contraction wire 35 has a proximal end anchored in the control handle 16, which is used to manipulate the contraction wire as described further below. The contraction wire 35 extends through the central lumen 18 of the catheter body 12, through the third lumen 32 of the intermediate section 14 and into the non-conductive cover 52 of the mapping assembly 17. The portion of the contraction wire 35 extending through the non-conductive cover 52 is positioned on the side of the generally circular main region 39 closer to the center of the generally circular main region, as best shown in FIG. 6. The center of the generally circular main region refers to the center of the circle formed by the generally circular main region. With this arrangement, contraction of the generally circular main region 39 is dramatically improved over arrangements where the position of the contraction wire 35 is not so controlled.

As shown in FIGS. 5 and 6, within the mapping assembly 17, the contraction wire 35 extends through a plastic tube 55. In one embodiment, the plastic tube 55 comprise three layers, including an inner layer of polyimide over which a braided layer is formed, the braided layer comprising a braided stainless steel mesh or the like, as is generally known in the art. The braided layer enhances the strength of the plastic tube 55, reducing the tendency for contraction wire 35 to straighten the preformed curve of the mapping assembly 17. A thin plastic layer of polytetrafluoroethylene is provided over the braided layer to protect the braided layer from getting tangled with the lead wires 40 within the non-conductive cover 52. The plastic tube 55 has a proximal end anchored to the distal end of the intermediate section 14 in the third lumen 32 by glue or the like (FIG. 8a). The support member 54 extends through the plastic tube 55 with the contraction wire 35 (FIG. 8a). The distal ends of the support member 54 and the contraction wire 35 are soldered or otherwise attached to a small stainless steel tube 53 (FIG. 7). With this arrangement, the relative positions of the contraction wire 35 and the support member 54 can be controlled so that the contraction wire can be positioned on the side of the generally circular region 39 closer to the center of the generally circular region 39, as described above. The contraction wire 35 on the inside of the curve pulls the support member 54 to the inside of the curve, enhancing contraction of the generally circular region 39. Further, when the plastic tube 55 includes a braided layer, it keeps the contraction wire 35 from tearing through the non-conductive cover 52.

A third compression coil 46 is situated within the catheter body 12 and intermediate section shaft 14 in surrounding relation to the contraction wire 35 (FIG. 2A). The third compression coil 46 extends from the proximal end of the catheter body 12 to near the distal end of the third lumen 32 of the intermediate section 14. The third compression coil 46 is made of any suitable metal, e.g., stainless steel, and is tightly wound on itself to provide flexibility, i.e., bending, but to resist compression. The inner diameter of the third compression coil 46 is preferably slightly larger than the diameter of the contraction wire 35. The outer surface of the compression coil 46 is covered by a flexible, non-conductive sheath 68, e.g., made of polyimide tubing. The third compression coil 46 can be formed of a wire having a square or rectangular cross-sectional area, which makes it less compressible than a compression coil formed from a wire having a circular cross-sectional area. As a result, the third compression coil 46 keeps the catheter body 12, and particularly the intermediate section 14, from deflecting when the contraction wire 35 is manipulated to contract the mapping assembly 17 as it absorbs more of the compression.

The third compression coil 46 is anchored at its proximal end to the outer wall 20 of the catheter body 12 by the proximal glue joint 50 and to the intermediate section 14 by distal glue joint 72.

It is understood that glue joints throughout the catheter 10 may comprise polyurethane glue or the like. The glue may be applied by means of a syringe or the like through a hole made in the tubing walls. Such a hole may be formed, for example, by a needle or the like that punctures the tubing walls where the needle is heated sufficiently to form a permanent hole. The glue is then introduced through the hole to wick around the component(s) within the tubing to form a glue joint about the entire circumference of the component(s).

In the depicted embodiment of FIG. 7, the distal end of the mapping assembly 17 is sealed closed with a dome 51 of polyurethane glue or the like. A short ring 56, made of metal or plastic, and e.g., polyamide, is mounted within the distal end of the non-conductive cover 52. The short ring 56 prevents the distal end of the non-conductive cover 52 from collapsing, there by maintaining the diameter of the non-conductive cover at its distal end.

At the junction of the intermediate section 14 and the mapping assembly 17 as shown in FIGS. 8a and 8b, the non-conductive cover 52 is attached to the intermediate section 14 by glue or the like. The plastic tube 55 has its proximal end inserted and glued in the distal end of the intermediate section 14. The glue (not shown) from the plastic tube 55 can further serve to anchor the distal end of the third compression coil 46 in place within the third lumen 32. The support member 54 extends from the third lumen 32 into the plastic tube 55 within the non-conductive cover 52. The proximal end of the support member 54 terminates a short distance proximally from the distal end of the third lumen 32, approximately about 5 mm, so as not to adversely affect the ability of the intermediate section 14 to deflect. However, if desired, the proximal end of the support member 54 can extend proximally further into the intermediate section 14 and/or the catheter body 12.

The lead wires 40 attached to the ring electrodes 26 extend through the first lumen 30 of the intermediate section 14 (FIG. 2A), through the central lumen 18 of the catheter body 12, through the control handle 16, and terminate at their proximal end in a connector (not shown) which is connected to an appropriate monitor or other device for receiving and displaying the information received from the ring electrodes 26. The portion of the lead wires 40 extending through the central lumen 18 of the catheter body 12, control handle 16 and proximal end of the intermediate section 14 is enclosed within a protective sheath 62, which can be made of any suitable material, such as polyimide. The protective sheath 62 is anchored at its distal end to the proximal end of the intermediate section 14 by gluing it in the lead wire lumen 30 with polyurethane glue or the like to form glue joint 73.

The lead wires 40 are attached to the ring electrode 26 by any conventional technique. In one embodiment, each ring electrode 26 is mounted by first forming a hole in the non-conductive cover 52. An electrode lead wire 40 is fed through the hole, and the ring electrode 26 is welded in place over the lead wire and non-conductive cover 52.

With reference to FIG. 1, the control handle 16 comprises a generally elongated handle housing, which can be made of any suitable rigid material, such as plastic configured through a suitable molding process. In the illustrated embodiment, the housing includes two opposing halves 16a and 16b that generally mirror each other and are joined by glue, sonic welding or other suitable means along a longitudinal peripheral seam 28 around the housing. In the illustrated embodiment, the cross section of the handle 16 formed by the opposing halves changes along the length of the handle. A more distal portion 112 has a smaller, generally rectangular cross section. A mid-portion 114 has a larger, generally rectangular cross section. A more proximal portion 116 has a generally circular cross section.

Figure 9:
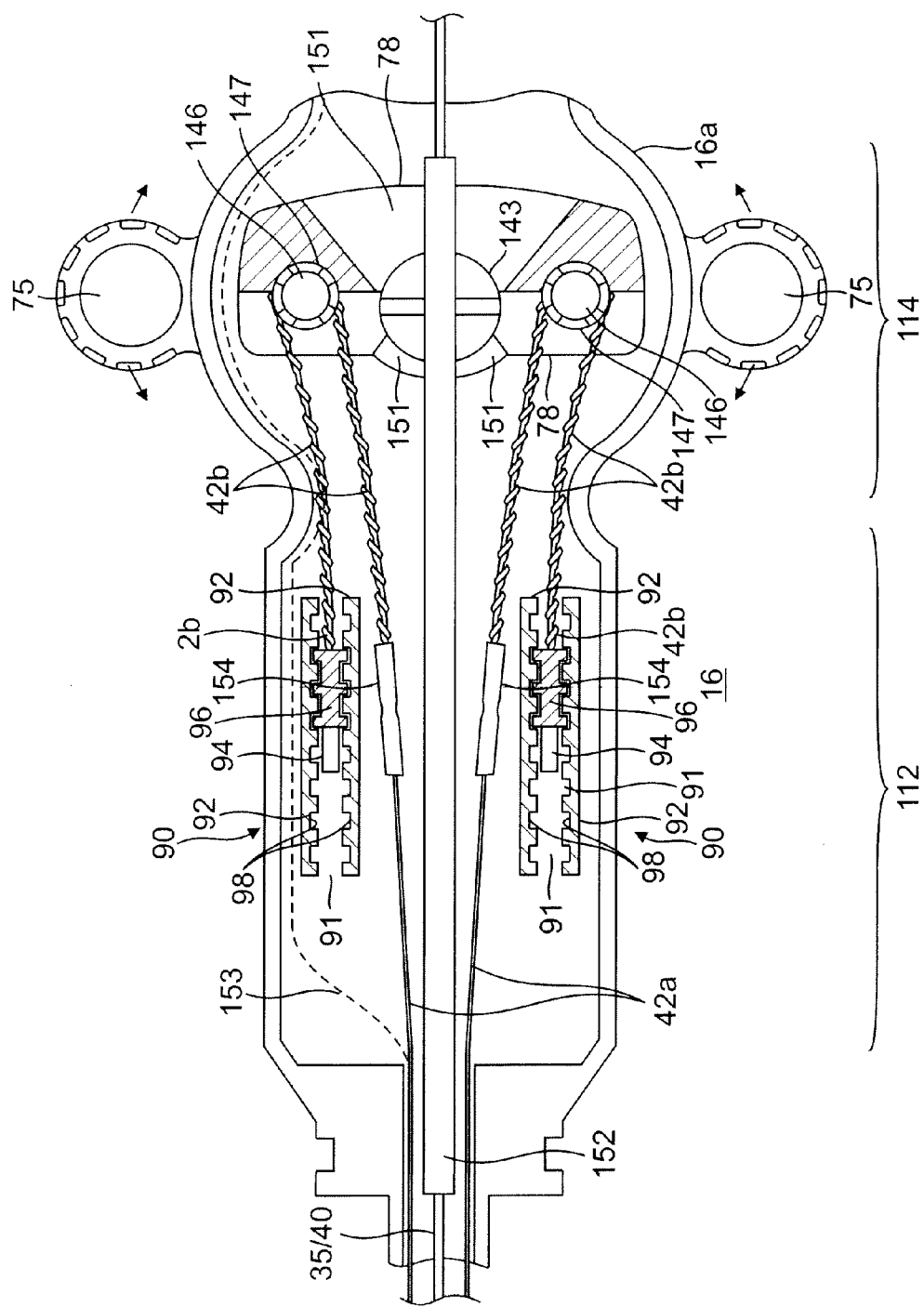
FIG. 9 is a top plan view of an embodiment of a control handle housing half including an embodiment of a deflection control assembly.

In the illustrated embodiment of FIGS. 1 and 9, the control handle 16 houses components of a deflection control assembly 74 in the mid-portion 114. The deflection control assembly includes a deflection member or arm 75 that can be directly manipulated by an operator to control deflection of the intermediate section 14. The deflection arm 75 is rotatable about an axis 76 that is generally transverse or perpendicular to the longitudinal axis of the control handle. The deflection control assembly 74 has a rotatable rocker member 78 that acts on the deflection puller members 42 to deflect the intermediate section 14.

Figure 10:
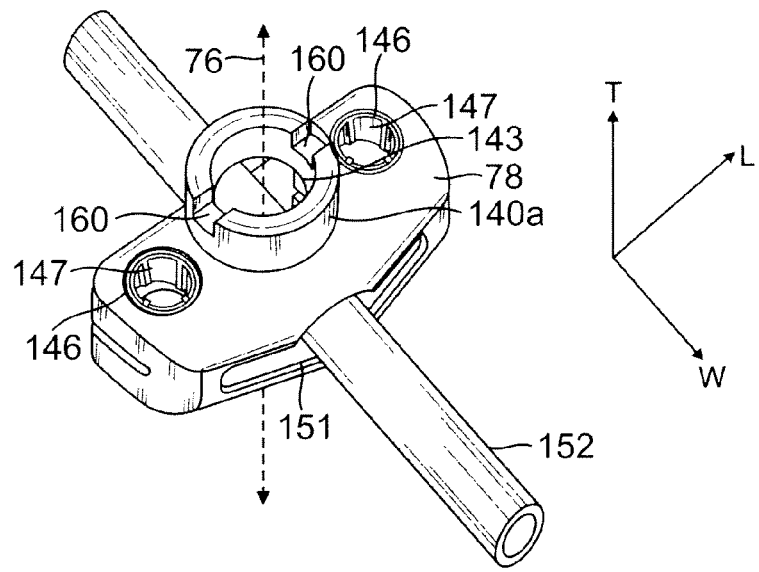
FIG. 10 is a top perspective view of an embodiment of a rocker member of a deflection control assembly.
Figure 11:
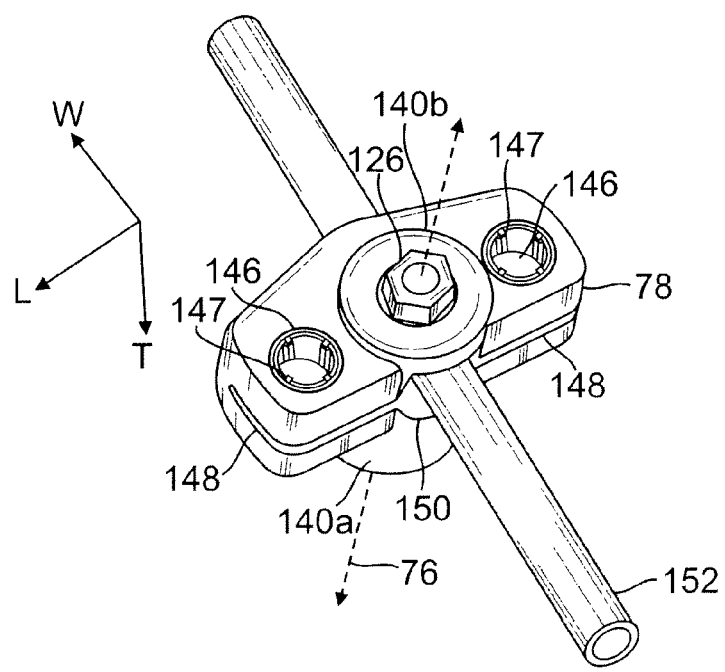
FIG. 11 is a bottom perspective view of an embodiment of a rocker member.
Figure 12:
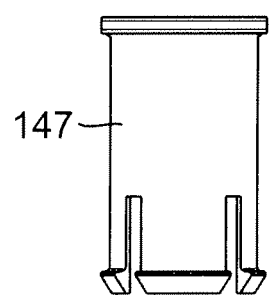
FIG. 12 is a side view of an embodiment of a pulley of a deflection control assembly.

The rocker member 78 has a length L dimension, a width W dimension and a thickness T dimension (FIGS. 10 and 11). Along its thickness dimension T, the rocker member 78 is configured with two opposing annular formations 140a and 140b that define a central hole or passage 143 that extends through its entire thickness. The central hole 143 is aligned with the rotational axis 76 of the deflection arm 75. Along its length dimension L, the rocker member 78 also has two smaller holes 146 that oppose each other across the central hole 143. In each hole sits a pulley 147, for example, a snap bearing (FIG. 12), that has a rotational axis parallel to the axis 76. Each deflection puller member 42 enters the rocker member through slots 148 and a portion is wound around a respective pulley 147.

Figures 13A, 13B, 13C:
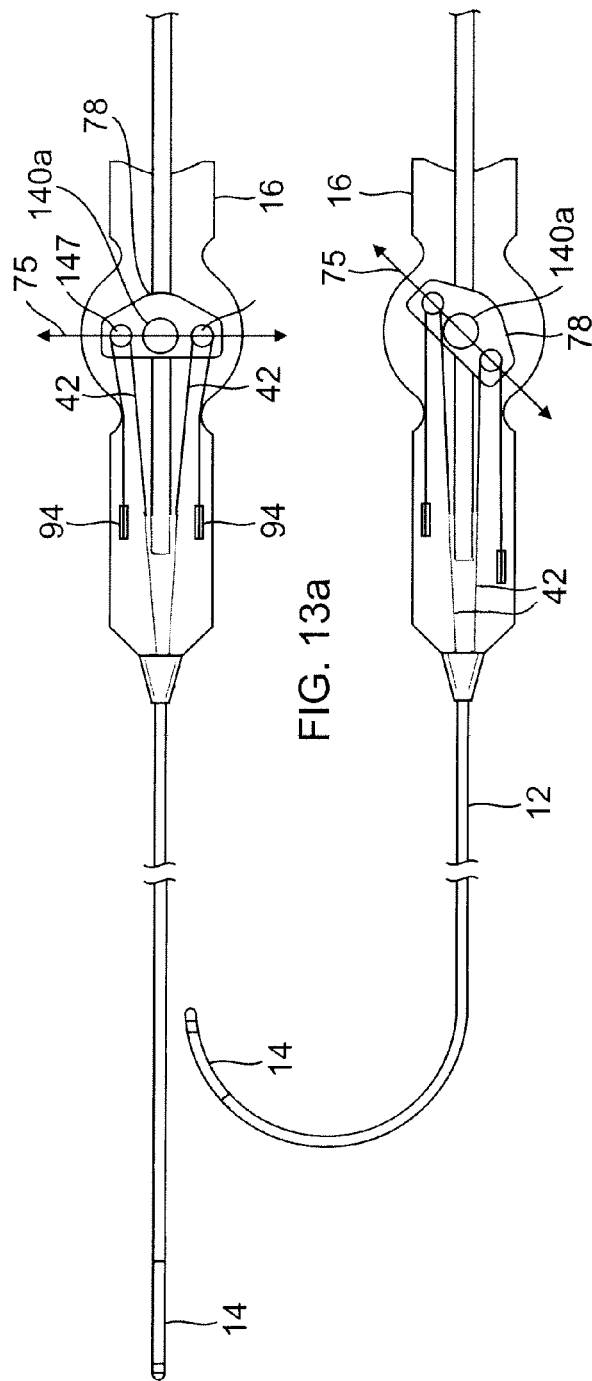
FIG. 13a-13c are schematics of an embodiment of the deflection control assembly in neutral and rotated configurations.

As understood by one of ordinary skill in the art, the rocker member 78 and the pulleys 147 are arranged such that rotation of the rocker member in one direction about the axis 76 draws back one puller member 42 to deflect the intermediate section 14 in that direction. With reference to FIGS. 13a-13c, as the rocker member 78 is rotated by means of the deflection arm (as represented by line 75), the pulleys 147 are displaced from a neutral position (FIG. 13a) with one pulley 147 drawing a puller member 42 on one side of the catheter body 12 against its anchored proximal end for deflecting the intermediate section 14 toward that side (FIGS. 13b and 13c).

Each deflection puller member 42 may comprise multiple segments. As illustrated in FIG. 9, each deflection puller member has a distal puller wire 42a and a proximal fiber 42b that are joined or connected at a location within the control handle 16 distal the rocker member 78. The puller wire 42a and the tensile fiber 42b of each deflection puller member are connected or secured to each other by a connector 154, e.g., a crimped brass ferrule covered by shrink tubing. Each puller wire 42a extends through the catheter body 12 and the intermediate section 14. Each tensile fiber 42b extends inside the control handle 16. In this manner, it is the more flexible tensile fibers 42b that interact with the pulleys 147 and undergo repeated bending and straightening during deflection operations, as they are less prone to bending stress and fatigue failure.

Each puller wire 42a is made of any suitable metal, such as stainless steel or Nitinol. Preferably each puller wire has a low friction coating, such as a coating of Teflon® or the like. Each puller wire has a diameter preferably ranging from about 0.006 inch to about 0.012 inch. Preferably both of the puller wires have the same diameter. Flat puller wires may be used in place of round puller wires. Their cross sectional dimensions should be such that they provide comparable tensile strengths as round puller wires.

Each tensile fiber 42b may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions.

In the illustrated embodiment of FIG. 9, each tensile fiber 42b extends proximally from the connector 154 toward the rocker member 78 where each is wound around a respective pulley 147 and turns about 180 degrees to double back toward the distal end of the control handle. Each proximal end of the tensile fiber 42b is anchored by an anchor assembly 90 that includes a pair or racks 92, a slug 94 and a stop 96. The proximal end of each tensile fiber 22b extends between a channel 91 defined by the pair of racks 92, and the proximal end of each tensile fiber is encased within a molded member or slug 94 sized to fit in and translate in the channel 91. Proximal the slug are the stops 96 that are adjustably positioned in a selected location along the racks 92, for example, by means of interlocking teeth 98 formed in the racks and the stops to releasably lock in the selected position against movement. The stops 96 are formed so that each respective tensile fiber 42b can slide through or below them while blocking the slugs 94 from moving proximally past them. Accordingly, the stops 96 limit the proximal movement of the slugs 94 and anchor the proximal ends of the tensile fibers 42b to effectuate deflection when each is drawn proximally by the deflection control assembly 74. During assembly of the control handle 16, before the two housing halves 16a, 16b are joined, the stops 96 are selectively positioned between the racks 92 to achieve a desirable tension in each tensile member. The interlocking teeth 98 of the racks 92 and stops 96 allow for fine adjustments in setting the tension.

Figure 14:
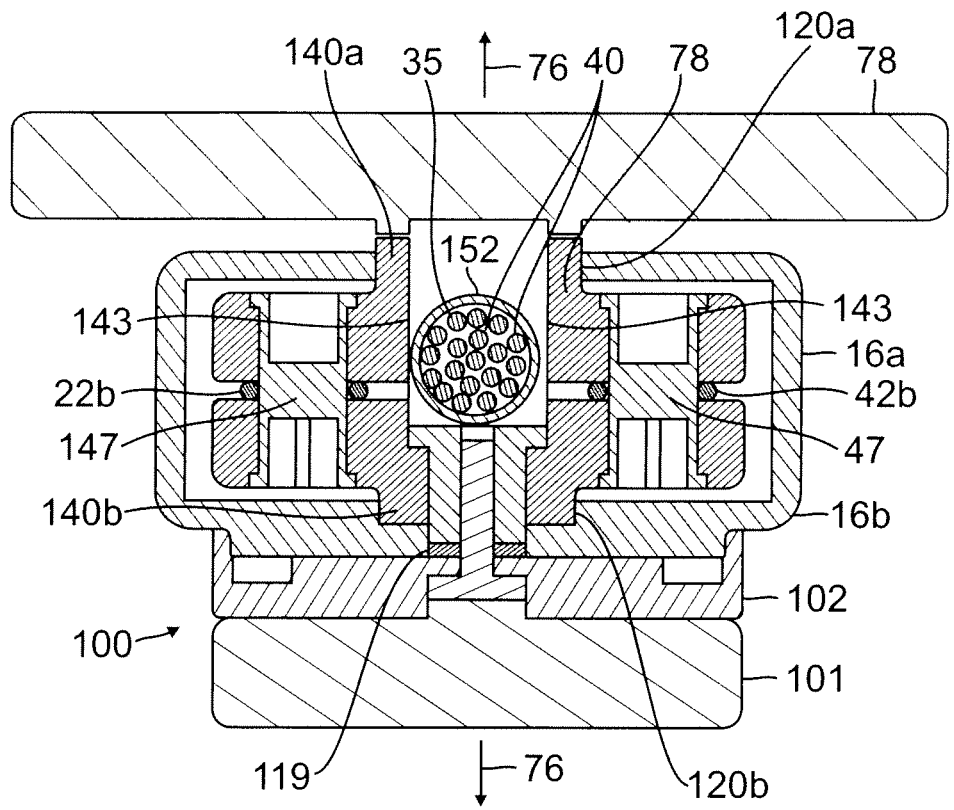
FIG. 14 is a longitudinal cross section of an embodiment of the deflection control assembly and tension control assembly mounted on a control handle.
Figure 14A:
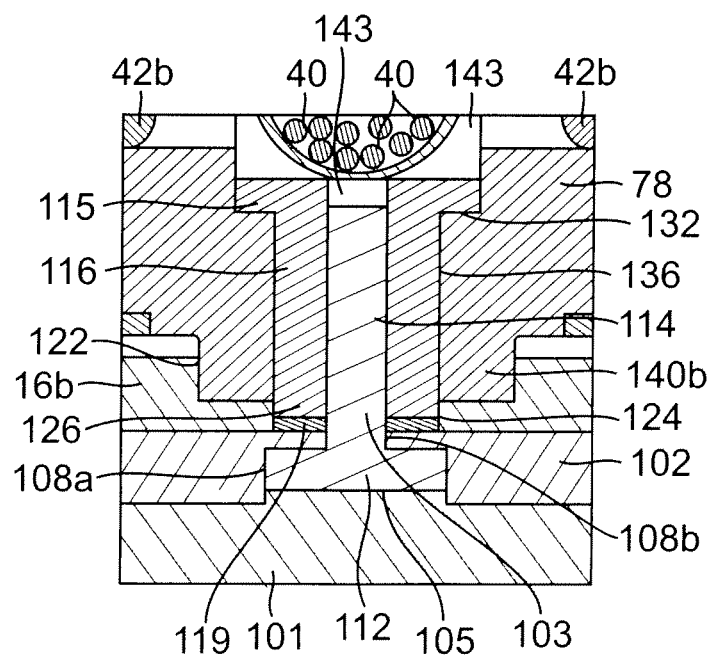
FIG. 14a is a detailed view of a portion of FIG. 14, including an embodiment of a retaining nut and a tension screw.

The construction and assembly of the deflection control assembly 74 including the deflection arm 75 and a tension adjustment member 101 on the control handle 16 are described as follows. With reference to FIGS. 14 and 14a, the rocker member 78 of the assembly 74 is situated between the two halves 16a and 16b of the control handle 16, with each of its annular formations 140a and 140b extending respectively through an opening 120a, 120b formed in the distal portion 114 of each housing half 16a and 16b.

Figure 15:
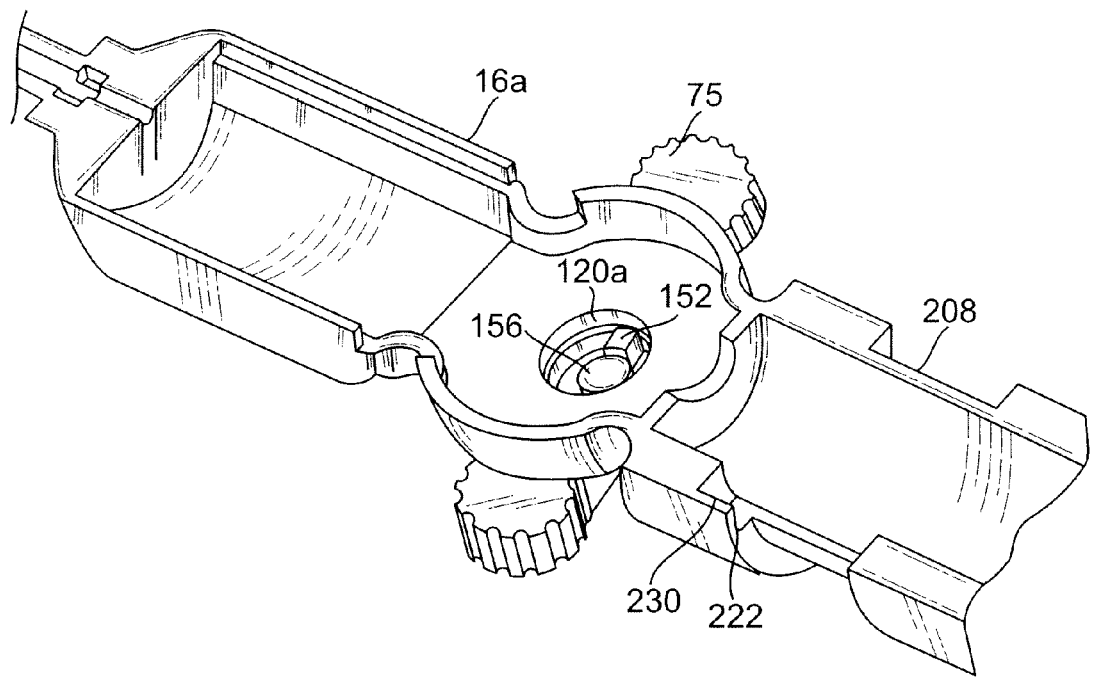
FIG. 15 is a partial perspective view of an embodiment of a first control handle housing half.
Figure 16:
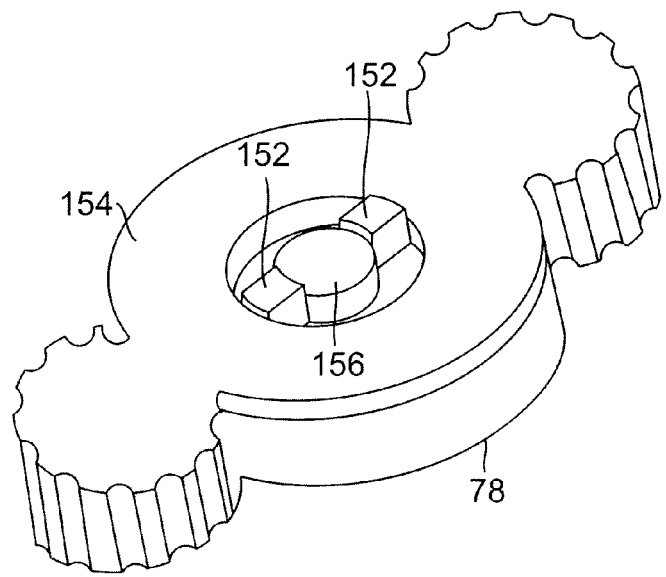
FIG. 16 is a perspective view of an embodiment of a deflection arm.

The annular formation 140a has recesses 160 (FIG. 10) exposed through the opening 120a (FIG. 15) that receive protrusions 152 projecting from a facing surface 154 of the deflection arm 75 (FIG. 16) to rotationally couple the deflection arm 75 and the rocker member 78. The protrusions 152 can snap fit into the recesses 160 and/or be secured by adhesives, glue, sonic welding and the like. A central circular protrusion 156 from the deflection arm 75 fits into the hole 143 circumscribed by the annular formation 140a of the rocker member 78. A suitable deflection assembly and control handle are described in co-pending U.S. application Ser. No. 12/346,834, filed Dec. 30, 2008, entitled DEFLECTABLE SHEATH INTRODUCER, the entire disclosure of which is hereby incorporated by reference. Another suitable deflection assembly with deflection sensitivity is described in co-pending U.S. application Ser. No. 12/211,728, filed Sep. 16, 2008, entitled CATHETER WITH ADJUSTABLE DEFLECTION SENSITIVITY, the entire disclosure of which is hereby incorporated by reference. Therein, a cam that is responsive to a deflection sensitivity knob can vary the separation distance between the two pulleys 147, thereby changing the deflection sensitivity of the deflection arm.

Opposing the deflection arm 75 is the deflection tension adjustment member or dial 101 (FIGS. 17 and 20) which is coupled to and indirectly engaged with the rocker member 78 by various mechanisms and parts and allows an operator to adjust the ease with which the deflection arm 75 can be rotated. Mounted primarily on the housing half 16b, the illustrated embodiment of a tension adjustment assembly 100 includes the adjustment dial 101 (FIG. 17), a locking plate 102 (FIG. 18), a tension cap screw 103, a retaining nut 136 and a washer 119 (see FIGS. 14 and 14a). A user rotates the dial 101 to adjust the tightness or tension of the rotational movement of deflection arm 75 by effectively compressing or releasing the rocker member 78 against the washer 119 (e.g., a Belleville type) and the control handle housing half 16b.

Figure 17:
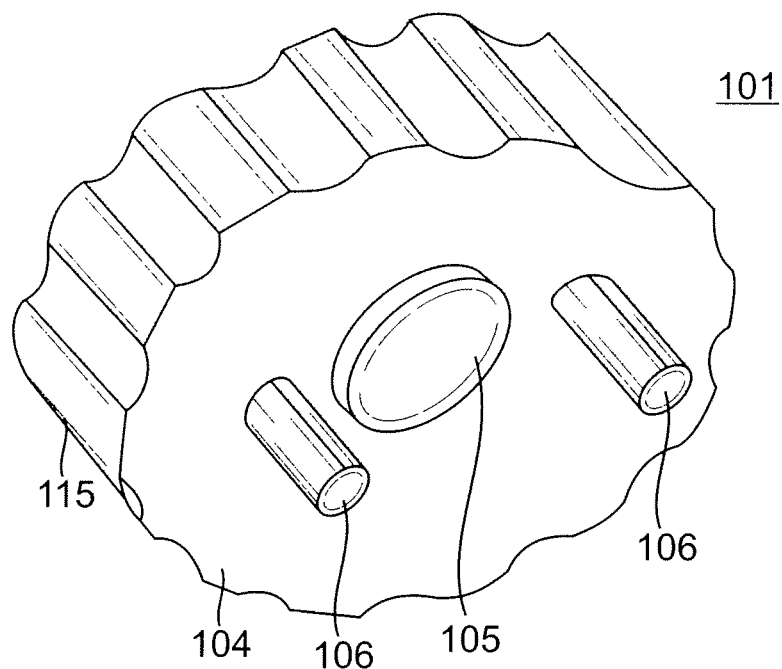
FIG. 17 is a perspective view of an embodiment of a tension control dial.
Figure 18:
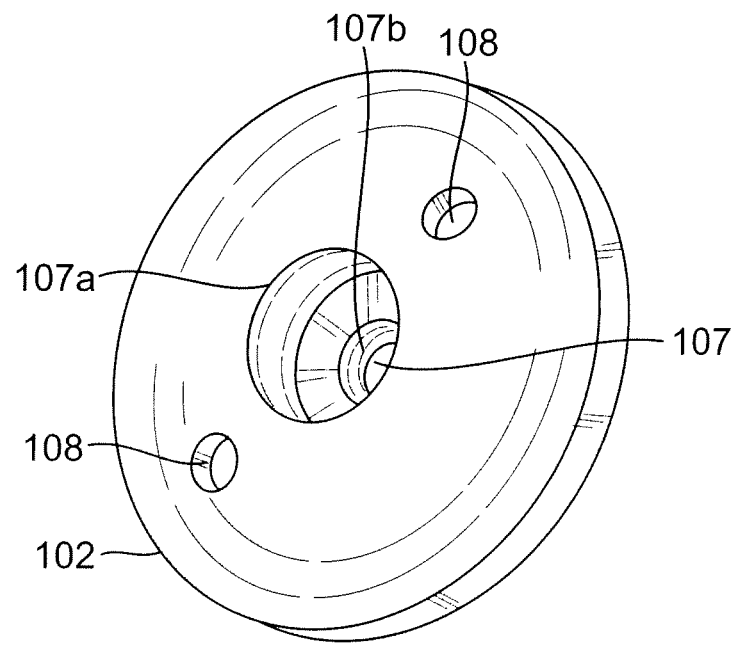
FIG. 18 is a perspective view of an embodiment of a locking plate.

The dial 101 has a generally circular cross section with a circumferential edge 115 having a friction-inducing surface (FIG. 17). A central circular protrusion 105 and a plurality of prongs 106 (FIG. 17) situated along a diameter of the dial project from a surface 104 of the dial 101.

Figure 20:
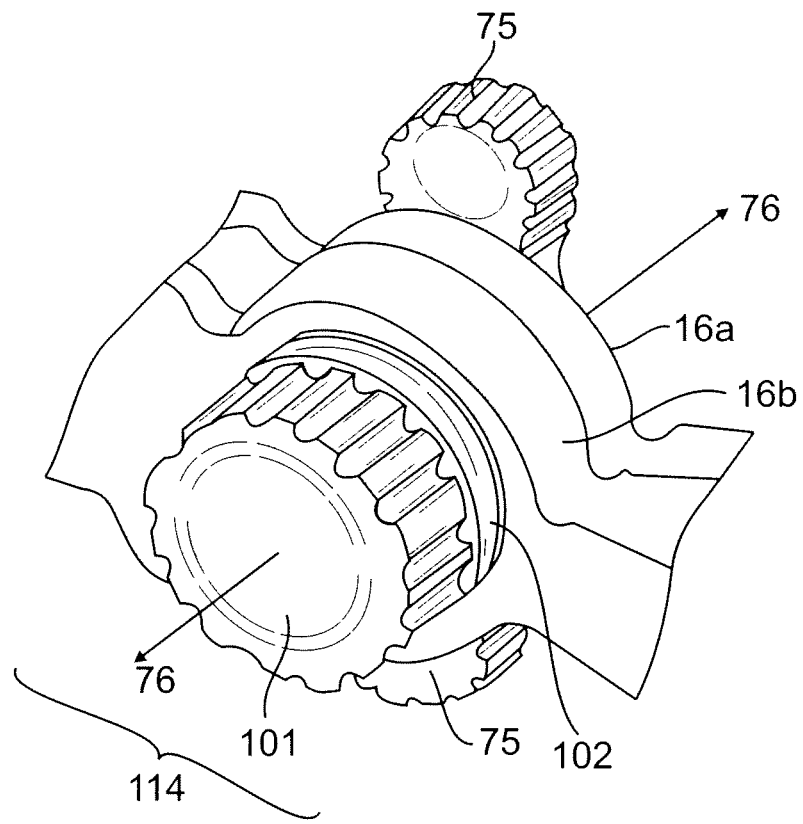
FIG. 20 is a partial perspective view of a portion of an embodiment of a deflection arm and a tension control member mounted on a control handle.
Figure 19:
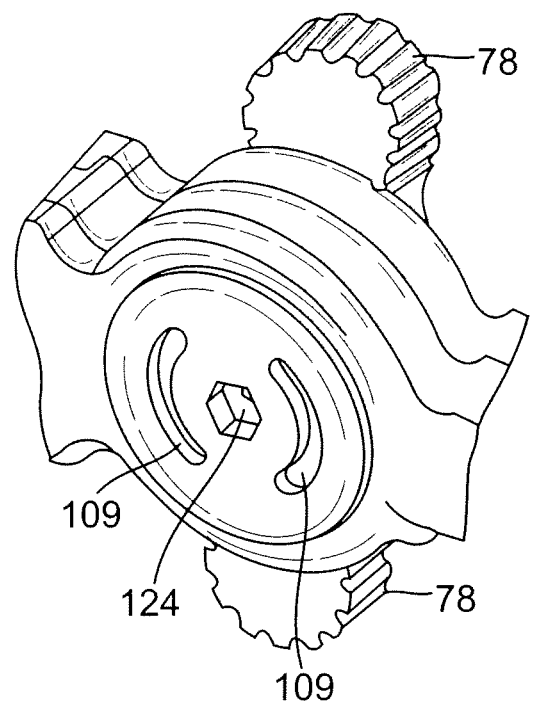
FIG. 19 is a partial perspective view of a portion of an embodiment of a control handle.
Figure 21:
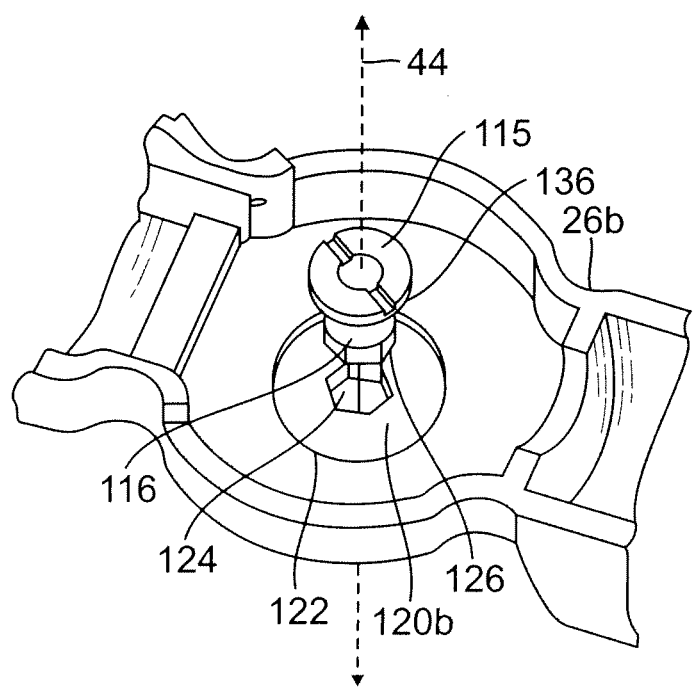
FIG. 21 is a partial perspective view of a portion of an embodiment of a second control handle housing half and a retaining nut, the second control housing half adapted to oppose the first control handle housing half.
Figure 22:
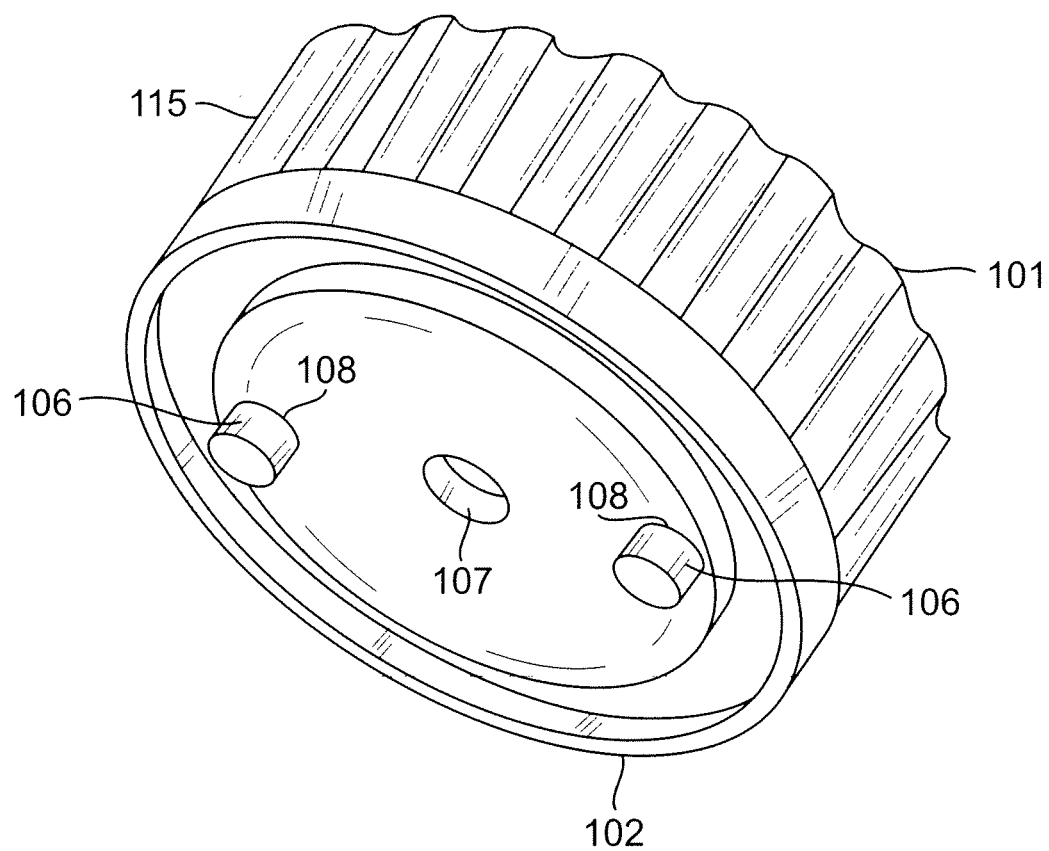
FIG. 22 is a perspective view of the tension control dial of FIG. 17 and locking plate of FIG. 18 as assembled.

The locking plate 102 is sandwiched between the dial 101 and the handle housing 16b (FIG. 20). The locking plate 102 (FIG. 18) has a central larger hole 107 and two smaller holes 108, all three of which extend through the entire thickness of the locking plate. The two prongs 106 of the dial 101 are adapted to be inserted through the smaller holes 108 in the plate 102 (FIG. 21) and received in semi-circular grooves 109 (FIG. 19) formed in an outer surface of the housing half 16b. The grooves 109 limit the degree of rotation of the dial 101 in clockwise and counterclockwise directions. The central hole 107 of the plate 102 (FIG. 18) has different cross-sections that include a larger circular cross-section 107a and a smaller circular cross-section 107b. The larger circular cross-section 107a receives a head 112 of a cap screw 103, and the smaller circular cross-section 107b receives a threaded body 114 of the cap screw 103 (FIG. 14a).

The threaded body 114 of the cap screw 103 extending through the central hole 107 of the locking plate 102 engages the retaining nut 136 situated in the opening 143 of the rocker member 78. A head 115 of the nut abuts and is anchored against a neck 132 formed in the inner surface of the opening 143 of the rocker member 78. The opening 120b in the housing half 16b (FIG. 21) has a larger cross section 122 and a smaller cross section 124. The smaller cross section 124 has a polygonal shape which matches a polygonal (e.g., hexagonal) end 126 of the nut 136 so that the nut 136 is effectively locked against rotation relative to the housing handle 16b.

The central protrusion 105 of the dial 101 (FIG. 17) forms a press or interference fit with the head 112 of the cap screw 103 to create rotational alignment between these two components. The prongs 106 of the dial 101 lock and rotationally couple the dial 101 and the lock plate 102, and the cap screw 103 is rotationally coupled to the locking plate 102. Coupling of the dial 101 and the locking plate 102 may also be achieved by means of welding the two components together. In that case, the prongs 106 need not protrude from the dial 101 but can instead extend from the locking plate 102.

Between the polygonal end 126 of the nut 136 and the housing handle 16b is the washer 119 whose compression against the nut 136 and the housing handle 16b is adjustable by the user's rotation of the dial 101 which tightens or releases the engagement between cap screw 103 and the nut 136, thus increasing or decreasing the ease with which the rocker member 78 and hence the deflection arm 75 can be rotated.

Components that extend through the control handle, including, for example, the lead wires 40 and the contraction wire 35 also enter the control handle at the distal end. In the illustrated embodiment of FIG. 9, these components extend along the longitudinal axis of the control handle. A protective tubing 152 through which the components extend can be provided, positioned between the two deflection puller members 42 and through a channel 150 form through the width dimension W of the rocker member 78 (FIG. 11). Distal and proximal portions of the channel 150 have indents, e.g., triangular or wedge-shaped, 151 (FIGS. 9 and 11) to allow the rocker member 78 to rotate freely within a predetermined range of angles, e.g., about ±45 degrees of the longitudinal axis of the control handle 16, without interference by the tubing 152 and the components therethrough.

Alternatively, the components extending through the control handle, with the exception of the contraction wire 35, are routed on an off-axis path 153 diverging from the deflection puller members 42 at entry into the distal end of the control handle 16. The components thus extend along the periphery of the housing handle, bypassing the rocker member 78.

It is understood that the distance between the distal end of the compression coils 44 and the distal anchor sites of each deflection puller members 42 in the intermediate section 14 determines the curvature of the intermediate section 14 in the direction of the deflection puller members. For example, an arrangement wherein the two deflection puller members 42 are anchored at different distances from the distal ends of the compression coils 44 allows a long reach curve in a first plane and a short reach curve in a plane 90.degree. from the first, i.e., a first curve in one plane generally along the axis of the intermediate section 14 before it is deflected and a second curve distal to the first curve in a plane transverse, and preferably normal to the first plane. The high torque characteristic of the catheter intermediate section 14 reduces the tendency for the deflection in one direction to deform the deflection in the other direction. Suitable deflection control handles and parts thereof for use with such a catheter are described in U.S. patent application Ser. No. 08/924,611, filed Sep. 5, 1997, entitled "Omni-Directional Steerable Catheter", Ser. No. 09/130,359, filed Aug. 7, 1998, entitled "Bi-Directional Control Handle for Steerable Catheter", and Ser. No. 09/143,426, filed Aug. 28, 1998, entitled "Bidirectional Steerable Catheter with Bidirectional Control Handle", the entire disclosures of which are hereby incorporated by reference.

Figure 23:
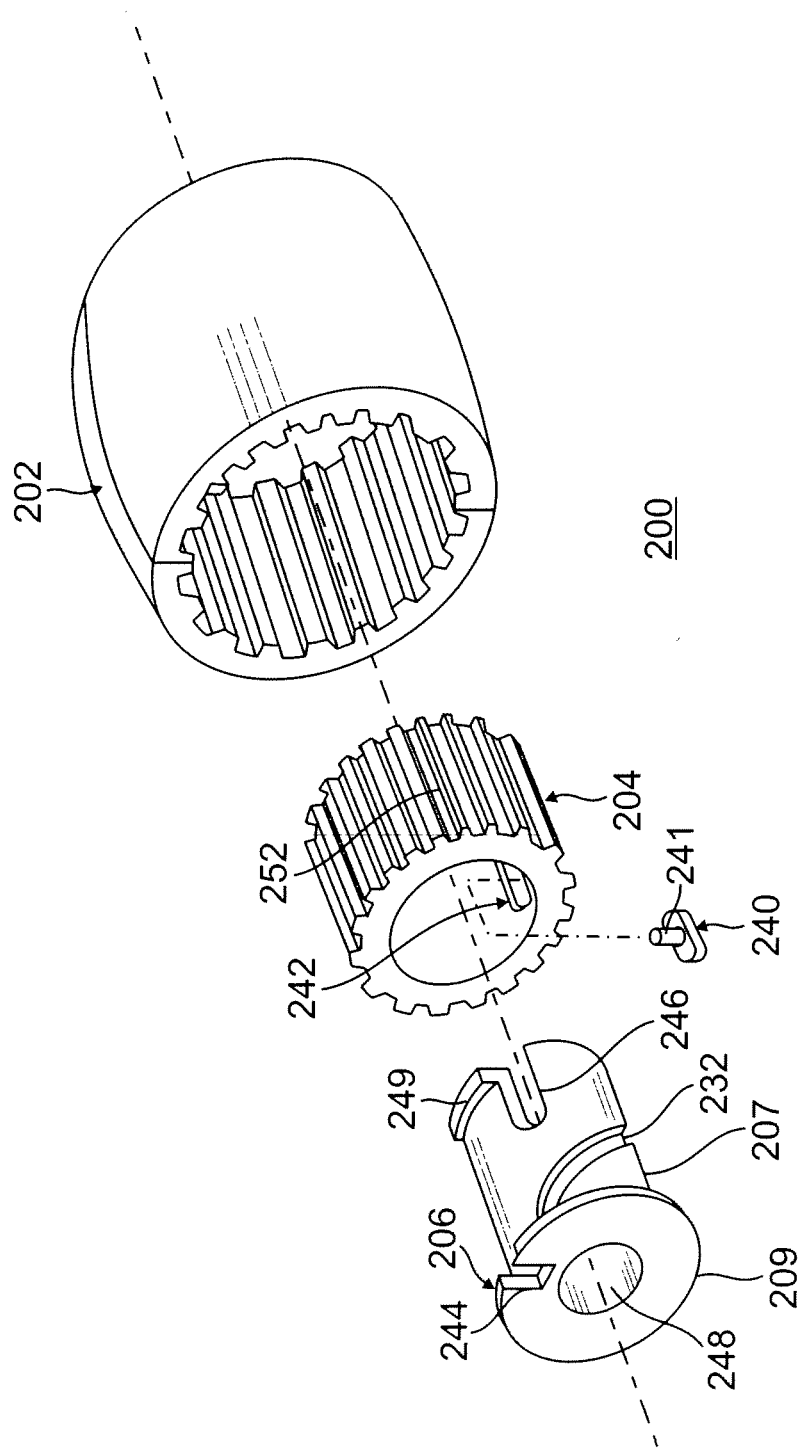
FIG. 23 is an exploded perspective view of an embodiment of a rotational control assembly.
Figure 24:
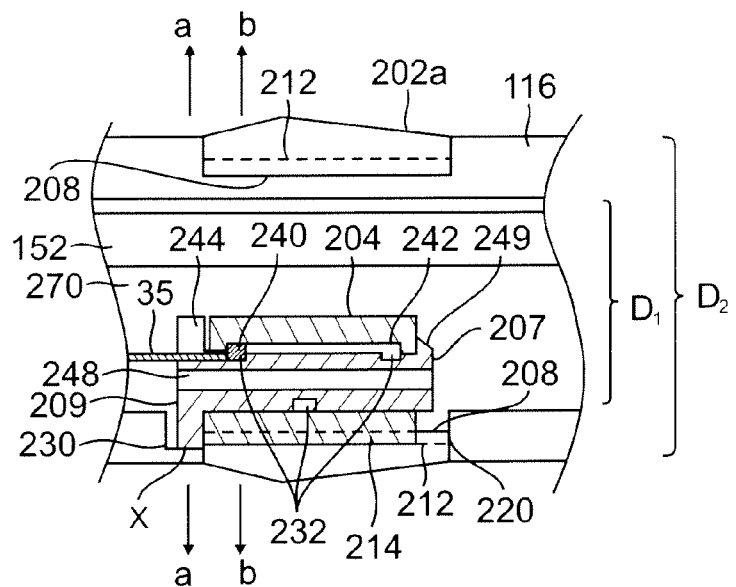
FIG. 24 is a side cross-sectional view of the rotational control assembly of FIG. 23, as assembled on a control handle.
Figure 26:
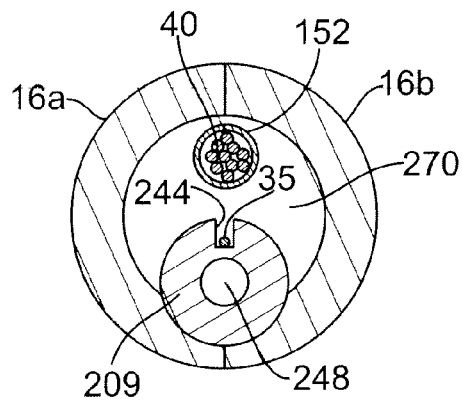
FIG. 26 is a longitudinal cross-sectional view of the rotational control assembly of FIG. 24, taken along line a-a.
Figure 25:
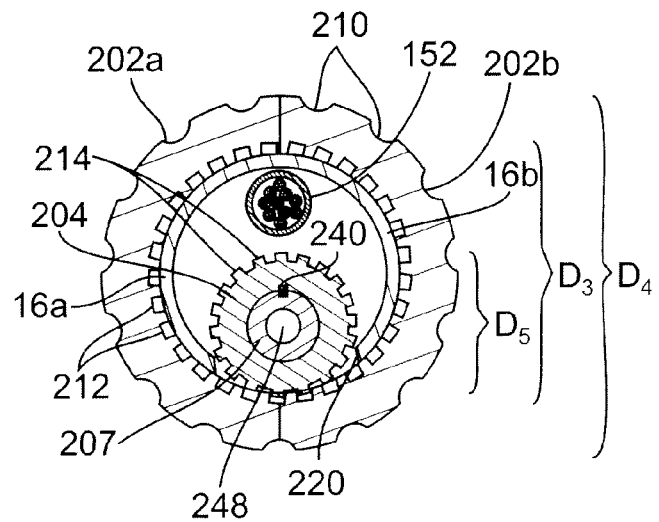
FIG. 25 is a longitudinal cross-sectional view of the rotational control assembly of FIG. 24, taken along line b-b.

For adjusting the mapping assembly 17 by means of a third puller member, e.g., the contraction wire 35, a distal end of the contraction wire extending between the two deflection puller members 42 within the control handle is anchored in the control handle for actuation by means of a rotational control assembly 200. In the illustrated embodiment of FIG. 23, the rotational control assembly 200 includes an outer rotational member (or control knob) 202, a cam 206 whose body 207 supports an inner rotational member (or gear) 204, the combination of which effectuates longitudinal movement of the contraction wire 35 relative to the catheter body 12, for example, to contract and expand the mapping assembly 17. With reference to FIGS. 23-25, the proximal portion 116 of the control handle 16 on which the rotational control assembly is mounted has a generally circular cross section of an inner diameter D1 and an outer diameter D2. In the disclosed embodiment, the rotational control assembly 200 is positioned proximal the deflection control assembly 74, although it is understood that it can be positioned distal the deflection control assembly 74.

In the disclosed embodiment, the outer rotational control knob 202 is mounted on the proximal portion 116 of the control handle. The knob 202 formed from two halves 202a, 202b adapted for snap-fit or joined by glue or sonic welding to each other is received in an outer circumferential recess 208 (see also FIG. 15) formed in the outer surface of control handle 16. The outer control knob 202 when assembled from the halves 202a, 202b is generally cylindrical, for example, in the shape of a ring, with an inner diameter D3 that is slightly greater than the recess 208 so that the knob 202 can be rotated around the control handle 16 within the recess 208. There can be circumferential contact between the knob 202 and the control handle 16 so long as the knob can be rotated in the recess 208. So mounted on the control handle, the knob is concentric with the proximal portion 116 of the control handle so that rotation of the knob is on axis with the longitudinal axis of the control handle. An outer surface of the knob has friction-inducing formations 210 to facilitate rotation of the knob 202 by a user of the catheter. A portion of the knob may have a diameter D4 that is greater than the outer diameter D2 of the handle.

The cam 206 on which the gear 204 is supported has a cylindrical body 207, and a collar 209 at a distal end. The gear 204 is mounted on the cylindrical body 207 of the cam so that the longitudinal axis of the cam 206 defines the rotational axis of the gear 204. The gear rotates on and about the cam 206. A portion of the collar 209 (e.g., a bottom portion in FIG. 23) is received in and affixed to a recess 230 (FIG. 15) formed in the inner surface of the control handle housing at a location X. The affixation of the collar 209 secures the cam 206 to the handle 16, and hence fixes the rotational axis of the gear 204 within and relative to the handle 16.

For rotationally coupling the knob 202 and the gear 204, for example, engaging and imparting rotational movement from the knob to the gear, inner surface of the knob 202 and outer surface of the gear 204 have formations such as interlocking teeth 212 and 214 (FIG. 24). In the illustrated embodiment, outer diameter D5 of the gear 204 is significantly smaller than the diameter D1 of the cross section of the handle 16 and the diameters D3 and D4 of the control knob 202, for example, by 50% or more, such that the axis of rotation of the gear 204 is off axis from the rotational axis of the knob 202 and the longitudinal axis of the control handle. Thus, only a portion of the teeth 212 and 214 engage each other at any one time.

The engagement between the teeth occurs through an opening or hole 220 (FIG. 24) formed in the handle 16 by the joinder of radial cutouts 222 (FIG. 15) in the two control handle housing halves 16a and 16b. It is understood that the opening 220 is not limited to the location illustrated but can be at any location around the circumference of the handle 16. The opening 220 in the handle 16 through which the teeth 212, 214 of the gear 204 and the outer ring 202 intermesh is immediately adjacent to the location X of the collar 209. In the illustrated embodiment, the opening 220 is immediately proximal the location X, although it is understood that the cam 206 can be reversed such that the collar 209 and location X are immediately proximal the opening 220.

Best seen in FIG. 23, a helical channel or track 232 is formed in the outer surface of the cylindrical body 207 of the cam 206, extending between the collar 209 and a proximal end of the cylindrical body. Riding in the track is a finger 241 of a follower 240 situated generally between the cam and the gear, whose movement is guided by an axial slot 242 formed in the gear 204 as the gear is rotated by the knob 202. A distal end of the contraction wire 35 is anchored to the finger 241 so that the follower draws the contraction wire 35 longitudinally relative to the catheter body 12. As a user rotates the knob 202, the gear 204 rotates along with its axial slot 242 and the follower 240 therein, each orbiting the longitudinal axis of the control handle 16. As the follower 240 orbits, it slides in the helical channel 232 as guided by the axial slot 242 to move distally or proximally relative to the control handle 16. As the follower 240 slides distally, the contraction wire 35 is drawn distally. As the follower 240 slides proximally, the contraction wire is pushed proximally. Such is a means by which rotational movement of the outer control knob 202 is converted to a longitudinal movement of the contraction puller member 35. Advantageously, the distance the follower 240 can travel along the helical track 232 is not limited to and in fact can be much greater than the length of the cylindrical body 207, for greater range or degree of motion in the catheter component controlled by the contraction wire 35. Indeed, the distance the follower 240 can travel (and hence amount by which the contraction wire 35 can be moved) along the cylindrical body 207 depends on the pitch of the helical track 232 (e.g., width of one complete helix turn) and the diameter of the cylindrical body 207. Accordingly, the control knob 202 is designed for rotation of at least 360, if not greater.

The collar 209 of the cam 206 has a radial notch 244 through which the contraction wire 35 passes to reach the body 207. A lip 249 is formed at the proximal end of the body 207 of the cam 206 as a snap-fit feature to retain the gear 204 on the body 207. Axial notches 246 allow deflection of the proximal end of the cam 207 to facilitate the snap-fit feature. Lead wires and other components (e.g., thermocouple wires, cables, irrigation tubing) extending through the protective tubing 152 can pass through passage 270 between the gear 204 and the knob 202.

Figure 27:
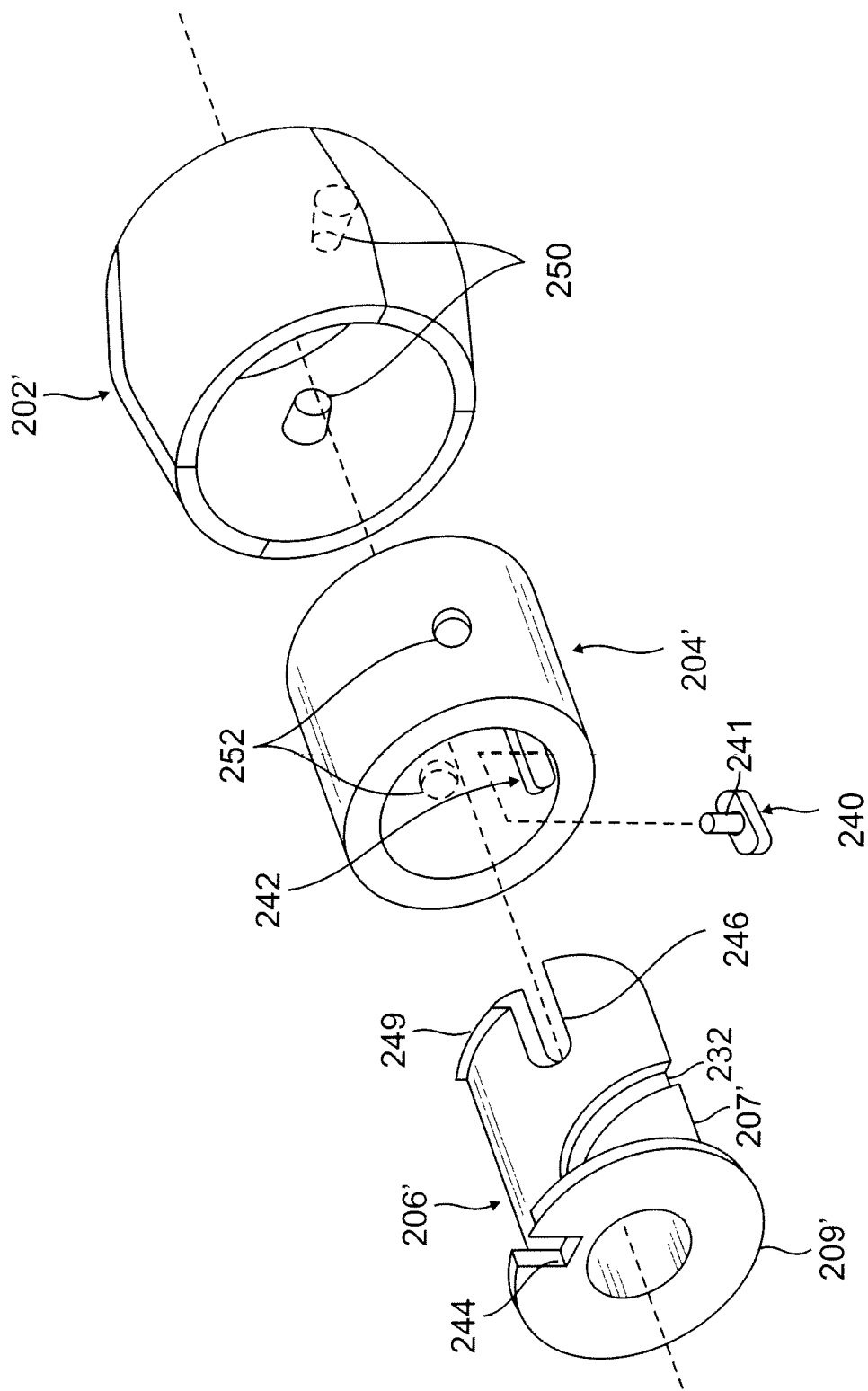
FIG. 27 is an exploded perspective view of an alternate embodiment of a rotational control assembly.
Figure 28:
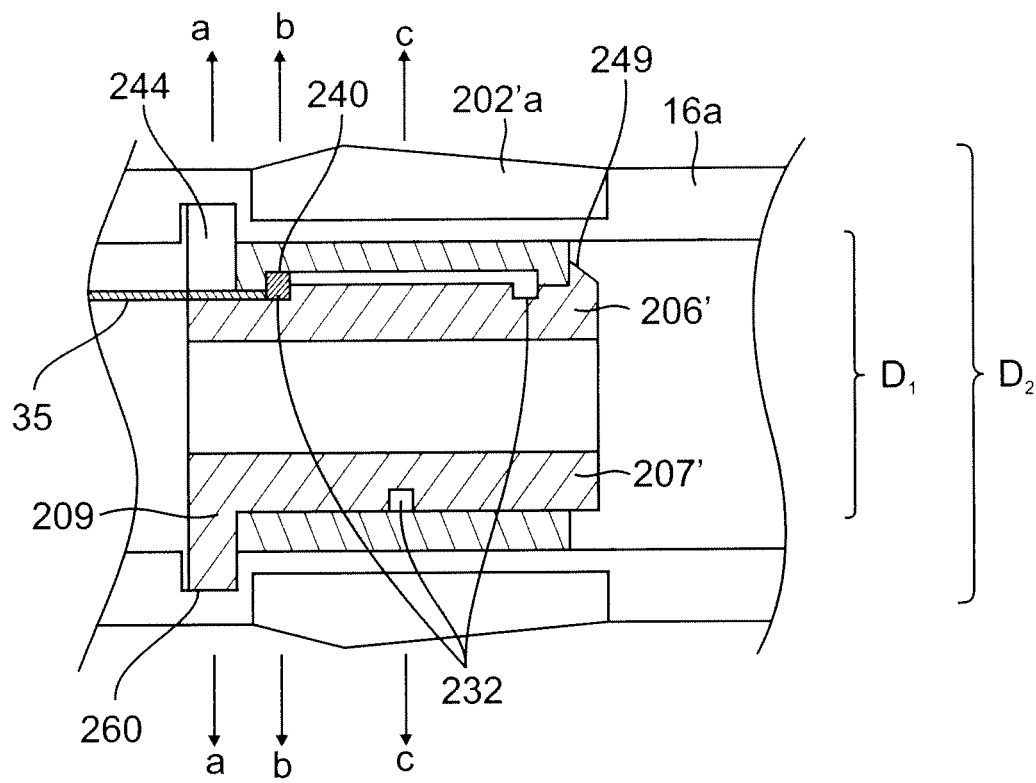
FIG. 28 is a side cross-sectional view of the rotational control assembly of FIG. 27, as assembled on a control handle.
Figure 29:
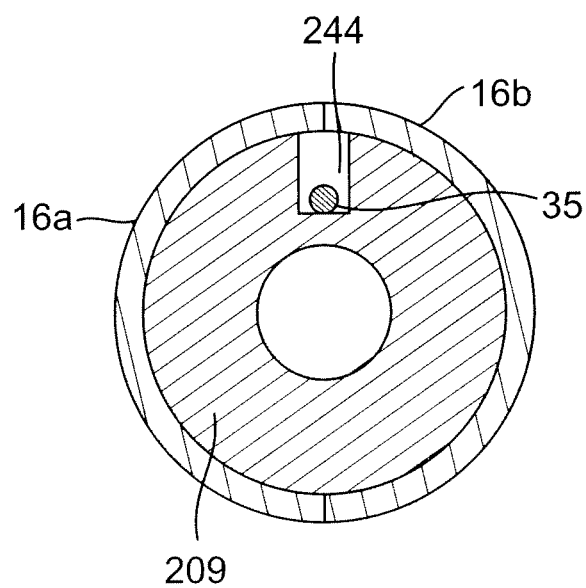
FIG. 29 is a longitudinal cross-sectional view of the rotational control assembly of FIG. 27, taken along line a-a.
Figure 30:
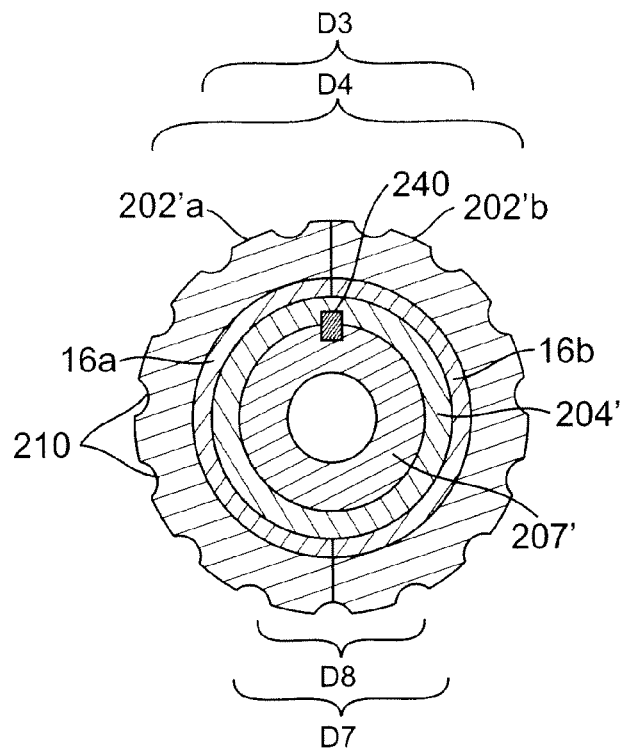
FIG. 30 is a longitudinal cross-sectional view of the rotational control assembly of FIG. 27, taken along line b-b.

In an alternate embodiment, a rotational control assembly 200' is illustrated in FIG. 27. Selected components are identical or similar; however, differences include a gearless outer rotational control knob 202', a larger, comparably-sized gearless inner rotational member 204' that is generally cylindrical, and a larger, comparably-sized cam 206', the latter two of which allow all three components to share a common longitudinal axis.

In the illustrated embodiment, the outer rotational control knob or ring 202' is mounted on the proximal portion 116 of the control handle 16'. The knob formed of two halves 202'a, 202'b is received in the outer circumferential recess 208 (FIG. 31) formed in the outer surface of the control handle housing halves 16a', 16W. The knob 202' is generally cylindrical, for example, in the shape of a ring, with an inner diameter D3 that is slightly greater the recess 208 so that the knob can be rotated within the recess 208. There can be circumferential contact between the knob 202' and the handle 16' so long as the knob can be rotated relative to the handle 16' about the longitudinal axis of the control handle. Likewise, an outer surface of the knob has friction-inducing formations 210 to facilitate rotation of the knob 202 by a user of the catheter. A portion of the knob may have a diameter D4 that is greater than the outer diameter D2 of the handle. However, the inner surface of the knob 202' is generally smooth.

In this embodiment, the cam 206' has a similar structure and function to the cam 206 of the foregoing embodiment with differences that include a larger outer diameter D8 of the cylindrical body 20T so that it can support the inner cylinder 204' in a generally on-axis or concentric position within the control handle and the outer knob 202' and allow the cylinder 204' and the outer knob 202' to have a common rotational axis. The collar 209' of the cam is fixed within a circumferential recess 260 formed in the inner surface of the control handle housing halves 16a', 16W.

For rotationally coupling the outer knob 202' and the inner rotational member 204', for example, for engaging and imparting rotational movement from the knob 202' to the inner rotational cylinder 204', the inner surface of the outer knob 202' and outer surface of the inner cylinder 204' have formations, e.g., fingers 250 formed in one that reach into matching indentations or holes 252 formed in the other. In the illustrated embodiment, there are at least two diametrically opposing fingers 250 formed in the inner surface of the outer knob 202' that engage with two diametrically opposing indents 252 formed in the outer surface of the inner rotational cylinder 204'. Thus, as illustrated, the inner cylinder 204' can have an outer diameter D7 that is slightly smaller than the inner diameter D1 of the proximal portion 116 of the control handle.

Figure 31:
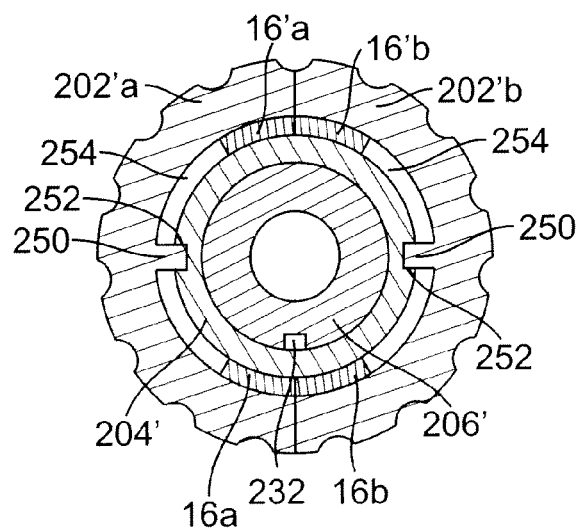
FIG. 31 is a longitudinal cross-sectional view of the rotational control assembly of FIG. 27, taken along line c-c.
Figure 32:
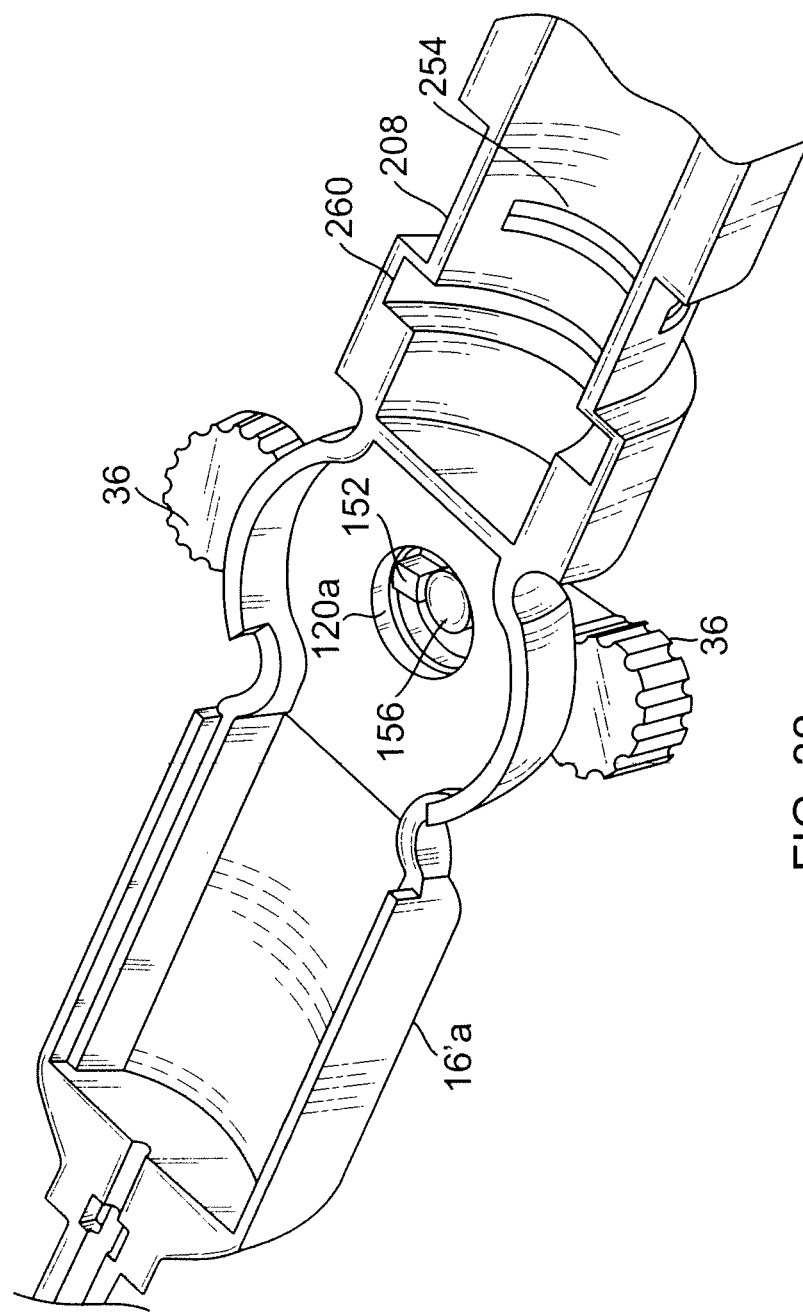
FIG. 32 is a partial perspective view of an alternate embodiment of a control handle housing half.

The engagement between the fingers 250 and the holes 252 occurs through a pair of diametrically opposing radial slots 254 formed in the handle housing halves 16a, 16b (FIG. 31). The slots 254 extend transversely to the longitudinal axis of the control handle. Where the handle has a circumference C, the length of the each of the two slots can be up to about 0.45 C, as the joining of the two slots would result in a discontinuity in the proximal portion 116 of the housing halves. As such, the outer knob 202' can be rotated up to about 290 degrees in the clockwise direction or in the counterclockwise direction. While it may be desirable to avoid a full circular slot, it is understood that the control handle can be constructed with a full circular slot yet have the proximal portion 116 remain connected to the mid and distal portions 112 and 114, for example, by internal structural connections therebetween. The angle of rotation achievable by this embodiment is dependent upon the plurality of fingers and the total material required to maintain adequate rigidity between the distal and proximal ends of the control handle 16.

As a user rotates the knob 202', the fingers 250 rotate the inner cylinder 204' which in turn rotates the axial slot 242 guiding the follower 240 to orbit about the cam 206'. The follower 240 in turn slides in the helical track 232 moving distally or proximally relative to the control handle. As the follower 240 slides distally, the contraction wire 35 is drawn distally, for example, to contract the mapping assembly 17. As the follower 240 slides proximally, the contraction wire 35 is pushed proximally, for example, to expand the mapping assembly 17.

It is understood that relative sizing of the components of the rotational control assembly is not limited to the illustrated embodiments. In the embodiment of FIGS. 22-25, the outer diameter of the gear 204 can range between about 0.2-0.9 of the inner diameter of the knob 202 so long as there is sufficient engagement in the teeth therebetween. In the embodiment of FIGS. 26-29, the outer diameter of the cylinder 204' can range between 0.2-0.9 of the inner diameter the knob 202' so long as the fingers are long enough to reach between the cylinder and the knob. For either embodiment, a suitable length L of the helical track about the cam body can be $L=Pi*(D_E-D_C)$ where $D_E$ is the expanded diameter of the generally circular main portion 39 of the mapping assembly 17 and $D_C$ is the contracted diameter of the generally circular main portion 39.

It is understood that the rotational control assembly uses a barrel-type cam to transform rotational movement of a control knob into useful linear deflection. The assembly components advantageously utilize minimal space to achieve desirable linear motions.

In use, a suitable guiding sheath is inserted into the patient with its distal end positioned at a desired mapping location. An example of a suitable guiding sheath for use in connection with the present invention is the Preface™ Braiding Guiding Sheath, commercially available from Biosense Webster, Inc. (Diamond Bar, Calif.). The distal end of the sheath is guided into one of the chamber, for example, the atria. A catheter in accordance with the present invention is fed through the guiding sheath until its distal end extends out of the distal end of the guiding sheath. As the catheter is fed through the guiding sheath, the mapping assembly 17 is straightened to fit through the sheath. Once the distal end of the catheter is positioned at the desired mapping location, the guiding sheath is pulled proximally, allowing the deflectable intermediate section 14 and mapping assembly 17 to extend outside the sheath, and the mapping assembly 17 returns to its original shape due to the shape-memory of the support member 54.

By manipulating and rotating the deflection arm 75 of the deflection control assembly 74 to deflect the intermediate section 14, the mapping assembly 17 is then inserted into a pulmonary vein or other tubular region (such as the superior vena cava, or inferior vena cava) so that the outer circumference of the generally circular main region 39 of the assembly 17 is in contact with a circumference inside the tubular region. Turning the deflection arm 75 in one direction deflects the intermediate section 14 to that direction. Turning the deflection 75 in the opposite direction deflects the intermediate section 14 to that opposite direction. Tension of the deflection 75 is adjusted by manipulating and rotating the dial 101. Turning the dial 101 in one direction increases the tension. Turning the dial 101 in the opposition direction decreases the tension. Preferably at least about 50%, more preferably at least about 70%, and still more preferably at least about 80% of the circumference of the generally circular main region is in contact with a circumference inside the tubular region.

The circular arrangement of the electrodes 26 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or the coronary sinus. By manipulating and rotating the outer control knob 202, 202' of the rotational assembly 200, the assembly 17, in particular, the generally circular main region 39, is contracted to fit the pulmonary vein or other tubular structure. By turning the knob in one direction, the contraction wire is drawn proximally to tighten and decrease the diameter of the generally circular region 39. By turning the knob in the opposition direction, the contraction wire is pushed distally to release the generally circular region 39 and expands its diameter.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   a catheter body;
   a deflectable intermediate section distal the catheter body;
   a mapping assembly distal the intermediate section, the mapping assembly having a generally circular portion;
   a control handle proximal the catheter body, the control handle having:
      a control handle housing;
      a deflection control assembly; and
      a rotational control assembly having an outer rotational member, an inner rotational member and a cam, the outer rotational member being in rotational engagement with the inner rotational member, the inner rotational member surrounding and being rotatably mounted on at least a portion of the cam, the cam being fixed to the control handle housing;
   first and second puller members responsive to the deflection control assembly adapted to deflect the intermediate section; and
   a third puller member responsive to the rotational control assembly, a proximal end of the third puller member anchored to the rotational control assembly such that rotation of the outer rotational member in a first direction moves the third puller member proximally to contract the generally circular portion of the mapping assembly and rotation of the outer rotational member in a second direction opposite the first direction moves the third puller member distally to expand the generally circular portion of the mapping assembly.

2. A catheter of claim 1,
   wherein the rotational control assembly further comprises a follower to which the proximal end of the third puller member is anchored, the follower being slidably received in an axial slot in the inner rotational member and extending into a track in the cam, and
   wherein the follower is adapted to slide in the track formed in the cam and the axial slot in the inner rotational member when the inner rotational member rotates.

3. A catheter of claim 2, wherein the track is helical on the cam.

4. A catheter of claim 2, wherein the outer and inner rotational members are rotationally coupled by formations extending therebetween.

5. A catheter of claim 4, wherein the formations are interlocking teeth.

6. A catheter of claim 4, wherein the formations are fingers extending from the outer rotational member into the inner rotational member.

7. A catheter of claim 1, wherein the inner rotational member and the outer rotational member have a common rotational axis.

8. A catheter of claim 1, wherein the outer rotational member has a first rotational axis and the inner rotational member has a second rotational axis offset from the first rotational axis.

9. A catheter of claim 8, wherein the first rotational axis is on axis with a longitudinal axis of the control handle.

10. A catheter of claim 1, wherein the rotational control assembly is proximal of the deflection control assembly.

11. A catheter of claim 1, further comprising a tension control assembly adapted to adjust tension of the deflection control assembly.

12. A multifunctional catheter control handle for use in a patient's heart, comprising:
   a control handle housing;
   a deflection control assembly having a deflection arm and a rocker member; and
   a rotational control assembly having an outer rotational member, an inner rotational member and a cam, the outer rotational member being in rotatable engagement with the inner rotational member, the inner rotational member surrounding and being rotatably mounted on at least a portion of the cam, the cam being fixed to the control handle housing;
   first and second puller members, each with a proximal end anchored to the deflection control assembly; and
   a third puller member with a proximal end anchored to the rotational control assembly such that rotation of the outer rotational member in a first direction moves the third puller member proximally and rotation of the outer rotational member in a second direction opposite the first direction moves the third puller member distally.

13. A control handle of claim 12, wherein the outer rotational member generally surrounds the inner rotational member and the inner rotational member is rotatably mounted on the cam,
   wherein the control assembly includes a follower to which the proximal end of the third puller member is anchored, the follower being adapted to follow the movement of the inner rotational member so as to slide in a track formed on the cam.

14. A control handle of claim 13, wherein the track is helical on the cam.

15. A control handle of claim 13, wherein the outer and inner rotational members are rotationally coupled by formations extending therebetween.

16. A control handle of claim 15, wherein the formations are interlocking teeth.

17. A control handle of claim 15, wherein the formations are fingers.

18. A control handle of claim 12, wherein the inner rotational member and the outer rotational member have a common rotational axis.

19. A control handle of claim 12, wherein the outer rotational member has a first rotational axis and the inner rotational member has a second rotational axis offset from the first rotational axis.

20. A control handle of claim 19, wherein the first rotational axis is on axis with a longitudinal axis of the control handle.

21. A control handle of claim 12, wherein the rotational control assembly is proximal of the deflection control assembly.

22. A control handle of claim 12, further comprising a tension control assembly adapted to adjust tension of the deflection control assembly.

* * * * *